US010045864B2

(12) United States Patent
Hes et al.

(10) Patent No.: US 10,045,864 B2
(45) Date of Patent: Aug. 14, 2018

(54) DYNAMIC TRIAL IMPLANTS

(71) Applicant: DePuy Synthes Products, Inc., Raynham, MA (US)

(72) Inventors: Robert Hes, Wilrijk (BE); Bart Conix, Zoersel (BE); Sean Saidha, Bellingham, MA (US); Cyril Baudouin, Hegenhein (FR); Christoph A Roth, West Chester, PA (US); Salman Chegini, Bern (CH)

(73) Assignee: Depuy Synthes Products, Inc., Raynham, MA (US)

( * ) Notice: Subject to any disclaimer, the term of this patent is extended or adjusted under 35 U.S.C. 154(b) by 149 days.

(21) Appl. No.: 14/744,300

(22) Filed: Jun. 19, 2015

(65) Prior Publication Data

US 2015/0282952 A1  Oct. 8, 2015

Related U.S. Application Data

(62) Division of application No. 12/783,111, filed on May 19, 2010, now Pat. No. 9,084,688.

(Continued)

(51) Int. Cl.
*A61B 17/70* (2006.01)
*A61F 2/46* (2006.01)
(Continued)

(52) U.S. Cl.
CPC .......... *A61F 2/4684* (2013.01); *A61F 2/4425* (2013.01); *A61F 2/4611* (2013.01);
(Continued)

(58) Field of Classification Search
CPC ........ A61F 2/46; A61F 2/4611; A61F 2/4603; A61F 2/4684; A61F 2/4657;
(Continued)

(56) References Cited

U.S. PATENT DOCUMENTS 5,782,925 A   7/1998  Collazo et al.
6,059,832 A   5/2000  Menon
(Continued)

FOREIGN PATENT DOCUMENTS

EP          1374807 A1       1/2004
WO    WO 2006/033067 A2     3/2006
WO    WO 2008/036417 A2     3/2008

OTHER PUBLICATIONS

International Patent Application No. PCT/US2010/035367: International Search Report dated Aug. 31, 2010, 8 pages.

*Primary Examiner* — Lynnsy Summitt
*Assistant Examiner* — Lynnsy Schneider
(74) *Attorney, Agent, or Firm* — Baker & Hostetler LLP

(57) ABSTRACT

A trial implant system including a trial implant configured to be temporarily inserted into an intervertebral space defined by a superior vertebral body and an inferior vertebral body is disclosed. The trial implant may include a superior plate and an inferior plate coupled to the superior plate. The superior plate may have a first mating portion that defines a first articulating interface and the inferior plate may have a second mating portion that defines a second articulating interface. The second articulating interface may be configured to interact with the first articulating interface of the superior plate such that at least one of the superior plate and the inferior plate is capable of movement relative to the other. The first and second articulating interfaces may be primary or auxiliary articulating interfaces. For example, the first and second articulating interfaces may be corresponding curved surfaces or they may be corresponding engagement features.

18 Claims, 28 Drawing Sheets

Related U.S. Application Data

(60) Provisional application No. 61/179,566, filed on May 19, 2009.

(51) Int. Cl.
   *A61F 2/44* (2006.01)
   *A61F 2/30* (2006.01)

(52) U.S. Cl.
   CPC .. *A61F 2/4657* (2013.01); *A61F 2002/30369* (2013.01); *A61F 2002/30378* (2013.01); *A61F 2002/4615* (2013.01); *A61F 2002/4629* (2013.01); *A61F 2002/4661* (2013.01); *A61F 2220/0033* (2013.01)

(58) Field of Classification Search
   CPC ...... A61F 2002/4625; A61F 2002/4668; A61F 2002/4658; A61F 2002/4659; A61F 2002/4661; A61F 2002/4662; A61F 2002/4663; A61F 2002/4664
   See application file for complete search history.

(56) References Cited

U.S. PATENT DOCUMENTS

| | | | |
|---|---|---|---|
| 6,723,097 B2 | 4/2004 | Fraser et al. | |
| 6,923,817 B2 | 8/2005 | Carson et al. | |
| 7,115,132 B2 | 10/2006 | Errico et al. | |
| 7,169,182 B2 | 1/2007 | Errico et al. | |
| 7,223,291 B2 | 5/2007 | Errico et al. | |
| 7,338,498 B2 | 3/2008 | Long et al. | |
| 7,803,162 B2 | 9/2010 | Marnay et al. | |
| 8,021,427 B2* | 9/2011 | Spoonamore | A61F 2/4611 623/17.14 |
| 8,105,381 B2 | 1/2012 | Marnay et al. | |
| 8,147,499 B2* | 4/2012 | Zubok | A61B 17/025 606/57 |
| 8,192,496 B2 | 6/2012 | Peukert et al. | |
| 8,231,677 B2 | 7/2012 | Duggal et al. | |
| 8,282,650 B2* | 10/2012 | Weber | A61F 2/4657 606/102 |
| 8,585,710 B2* | 11/2013 | Fischer | A61F 2/4657 606/102 |
| 9,216,098 B2* | 12/2015 | Trudeau | A61F 2/4657 |
| 9,381,098 B2* | 7/2016 | Gittings | A61B 17/025 |
| 9,386,975 B2* | 7/2016 | Markworth | A61B 17/025 |
| 2003/0069586 A1 | 4/2003 | Errico et al. | |
| 2003/0233097 A1 | 12/2003 | Ferree | |
| 2004/0087947 A1 | 5/2004 | Lim et al. | |
| 2004/0143331 A1 | 7/2004 | Errico et al. | |
| 2004/0148027 A1 | 7/2004 | Errico et al. | |
| 2004/0153158 A1 | 8/2004 | Errico et al. | |
| 2004/0167534 A1 | 8/2004 | Errico et al. | |
| 2004/0167535 A1 | 8/2004 | Errico et al. | |
| 2004/0167536 A1 | 8/2004 | Errico et al. | |
| 2004/0167537 A1* | 8/2004 | Errico | A61F 2/442 606/99 |
| 2004/0193275 A1 | 9/2004 | Long et al. | |
| 2004/0236342 A1* | 11/2004 | Ferree | A61B 17/025 606/102 |
| 2005/0038445 A1 | 2/2005 | Errico et al. | |
| 2005/0038516 A1 | 2/2005 | Spoonamore | |
| 2005/0055095 A1 | 3/2005 | Errico et al. | |
| 2005/0060035 A1 | 3/2005 | Errico et al. | |
| 2005/0071013 A1 | 3/2005 | Zubok et al. | |
| 2005/0154462 A1 | 7/2005 | Zucherman et al. | |
| 2005/0182416 A1* | 8/2005 | Lim | A61B 17/025 606/90 |
| 2005/0192671 A1 | 9/2005 | Bao et al. | |
| 2005/0216092 A1 | 9/2005 | Marik et al. | |
| 2006/0036327 A1 | 2/2006 | Enayati | |
| 2006/0167551 A1 | 7/2006 | Stad | |
| 2006/0241643 A1* | 10/2006 | Lim | A61B 17/025 606/90 |
| 2007/0010887 A1 | 1/2007 | Williams et al. | |
| 2007/0055378 A1 | 3/2007 | Ankney et al. | |
| 2007/0123985 A1 | 5/2007 | Errico et al. | |
| 2007/0156243 A1 | 7/2007 | Errico et al. | |
| 2007/0198092 A1 | 8/2007 | Errico et al. | |
| 2007/0208346 A1 | 9/2007 | Marnay et al. | |
| 2007/0260260 A1* | 11/2007 | Hahn | A61F 2/4657 606/102 |
| 2007/0270972 A1 | 11/2007 | Gordon et al. | |
| 2008/0058940 A1 | 3/2008 | Wu et al. | |
| 2008/0058944 A1 | 3/2008 | Duplessis et al. | |
| 2008/0065226 A1 | 3/2008 | Long et al. | |
| 2008/0082169 A1* | 4/2008 | Gittings | A61B 17/025 623/17.16 |
| 2008/0109001 A1 | 5/2008 | Hume et al. | |
| 2008/0109081 A1 | 5/2008 | Bao et al. | |
| 2008/0161823 A1 | 7/2008 | Klotz et al. | |
| 2008/0177299 A1 | 7/2008 | Kim et al. | |
| 2008/0221693 A1 | 9/2008 | Brehm et al. | |
| 2008/0269904 A1 | 10/2008 | Voorhies | |
| 2009/0018661 A1 | 1/2009 | Kim et al. | |
| 2009/0093882 A1 | 4/2009 | Oh et al. | |
| 2009/0163925 A1* | 6/2009 | Keller | A61B 5/1071 606/102 |
| 2009/0182343 A1* | 7/2009 | Trudeau | A61F 2/4657 606/102 |
| 2009/0281629 A1 | 11/2009 | Roebling et al. | |
| 2010/0292800 A1 | 11/2010 | Zubok | |
| 2010/0331988 A1 | 12/2010 | Marnay et al. | |

* cited by examiner

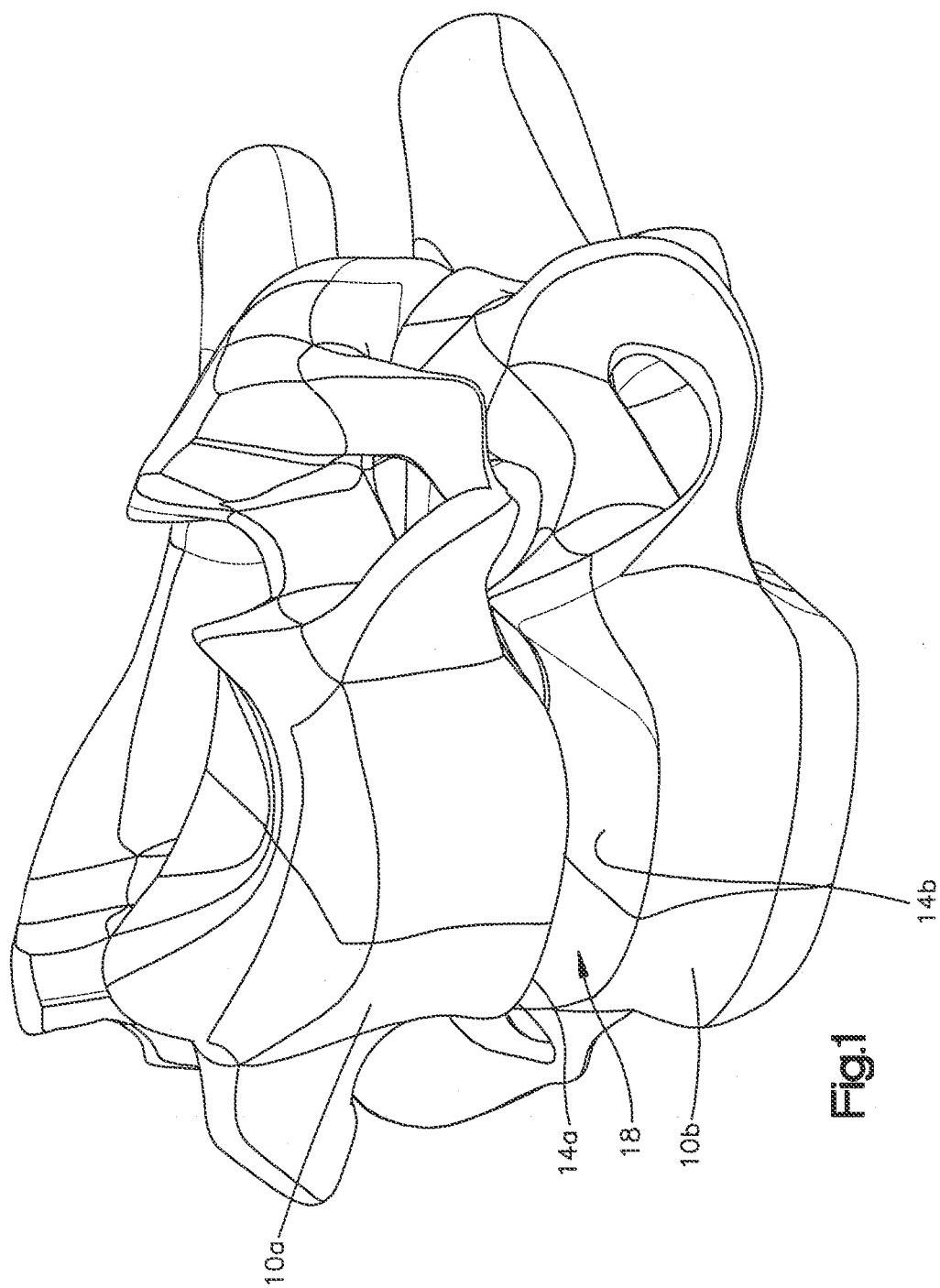

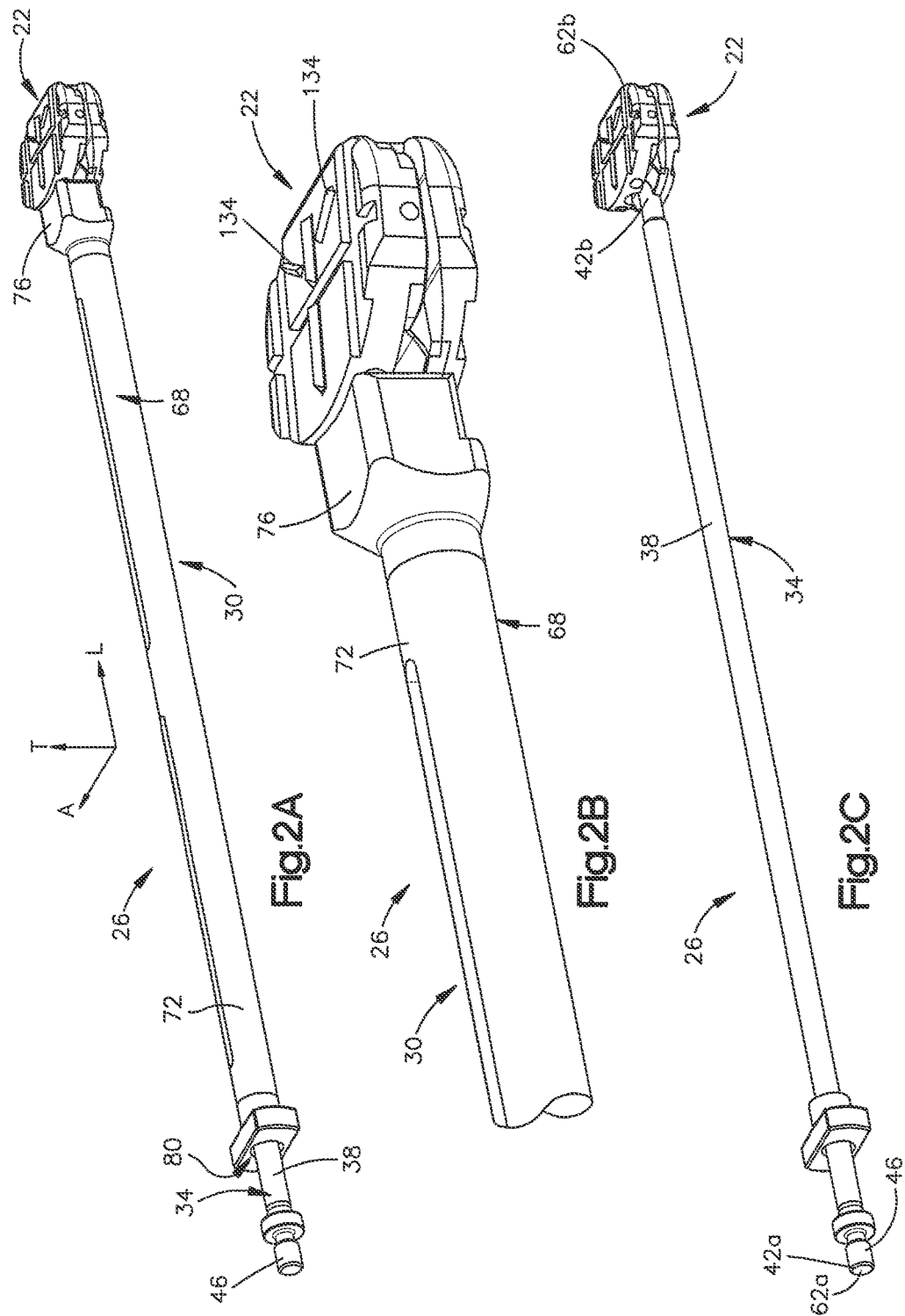

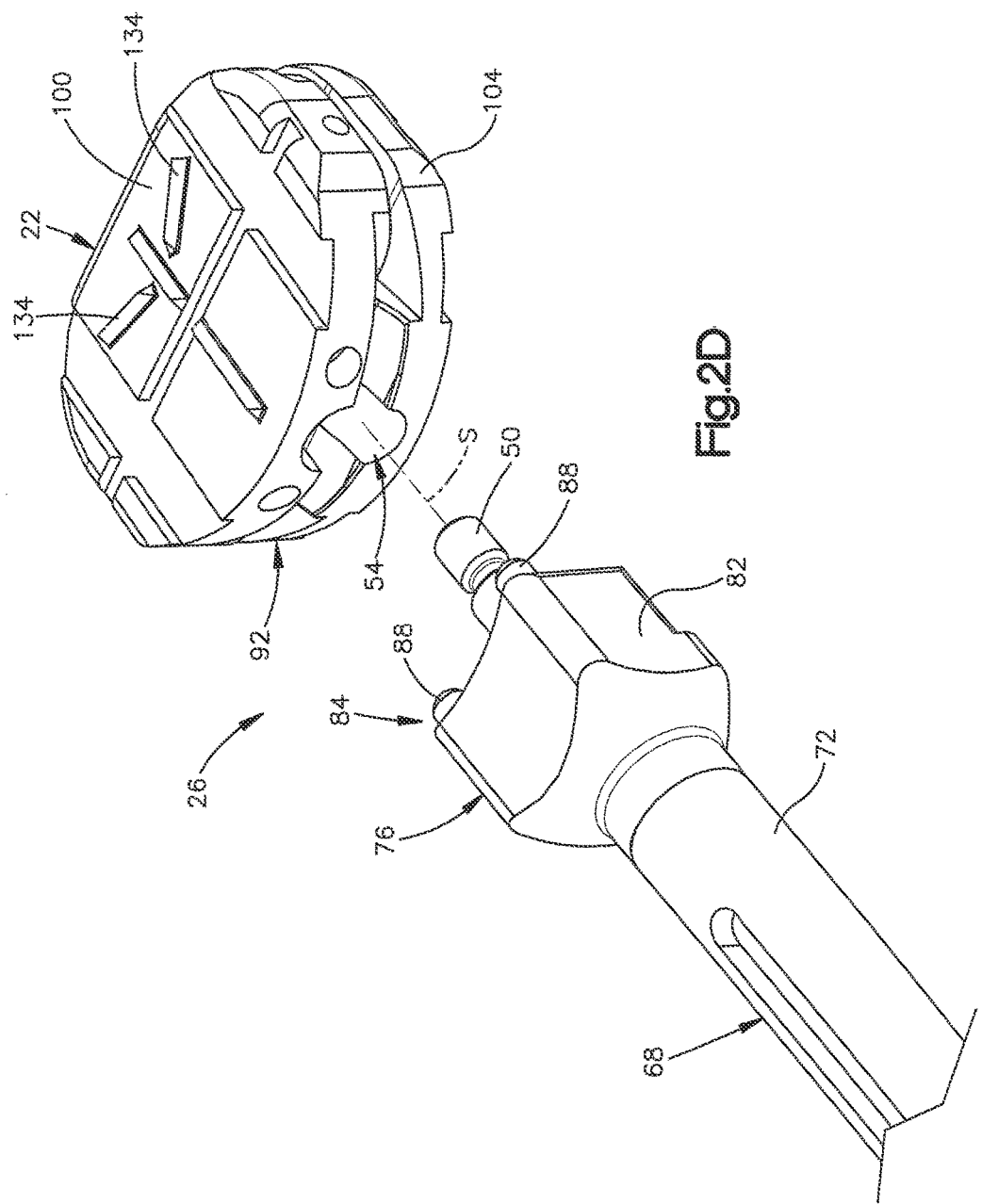

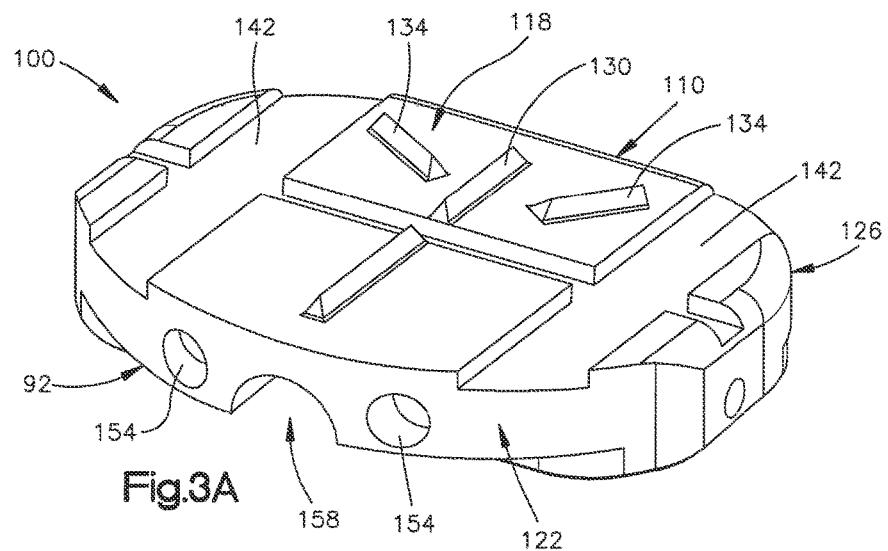
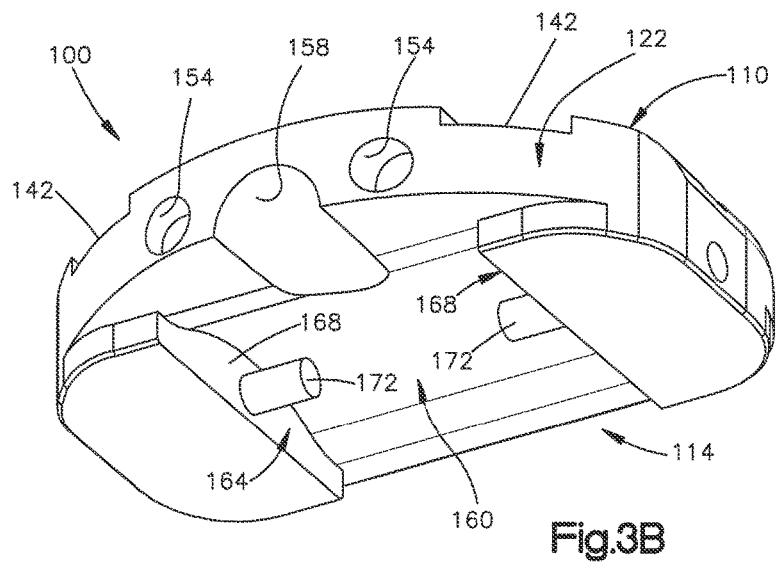

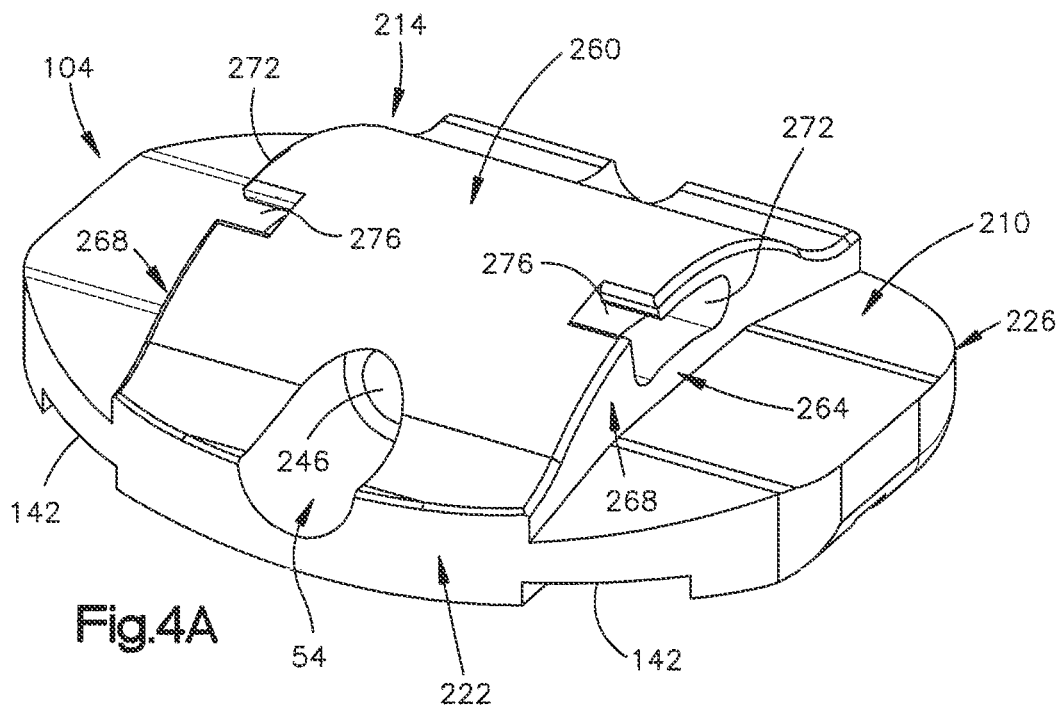
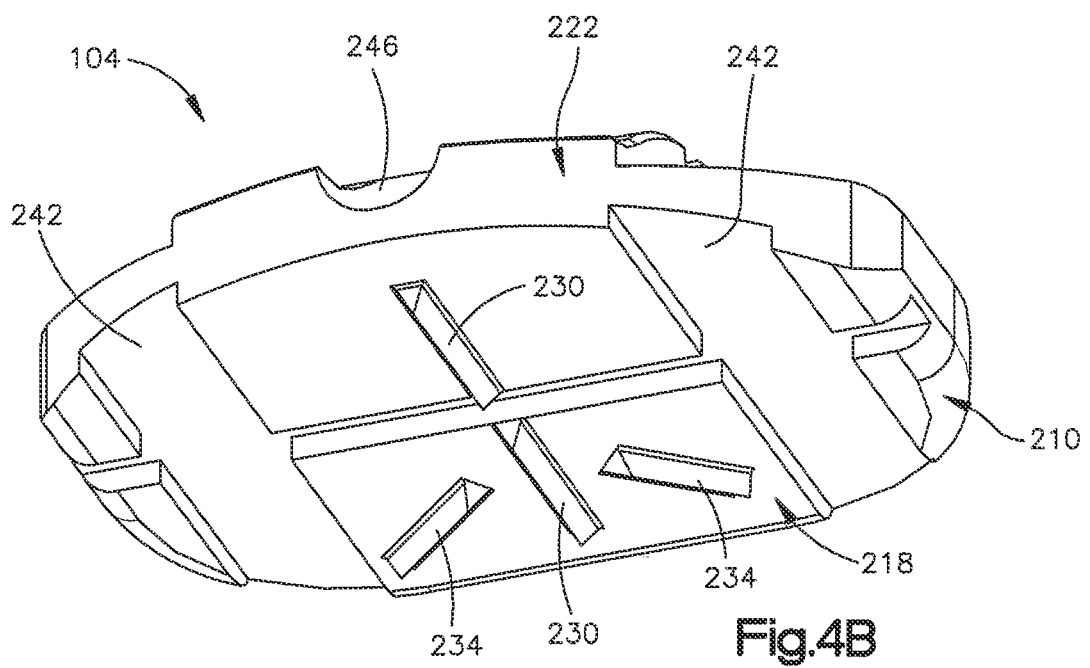

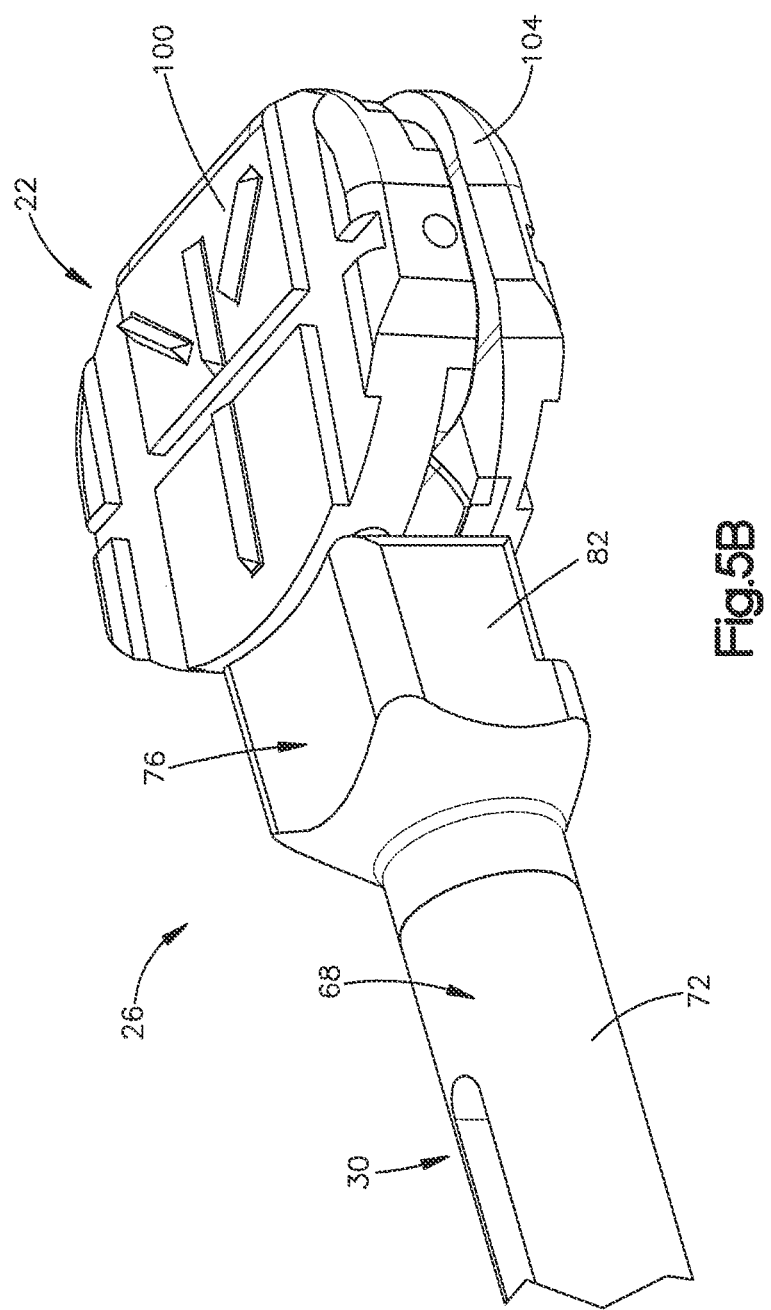

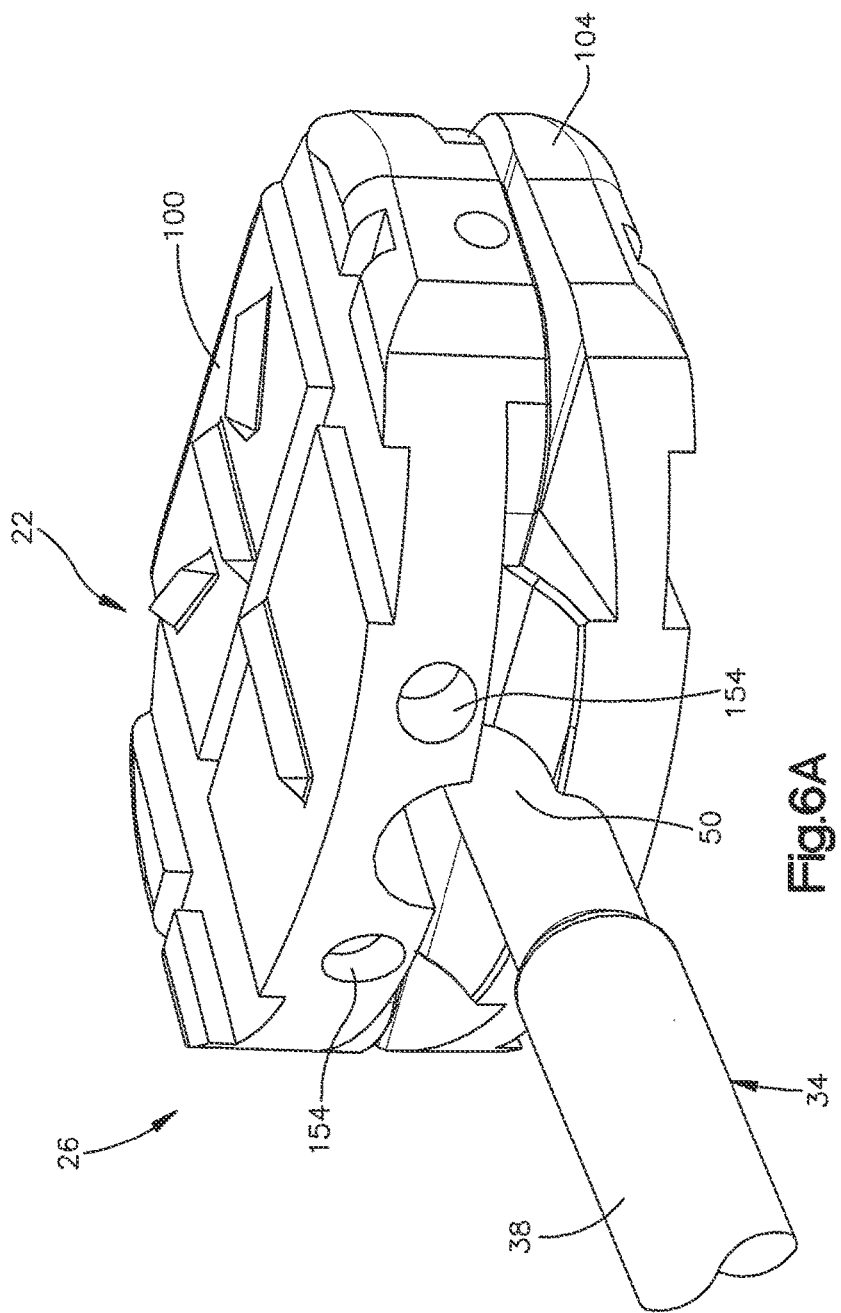

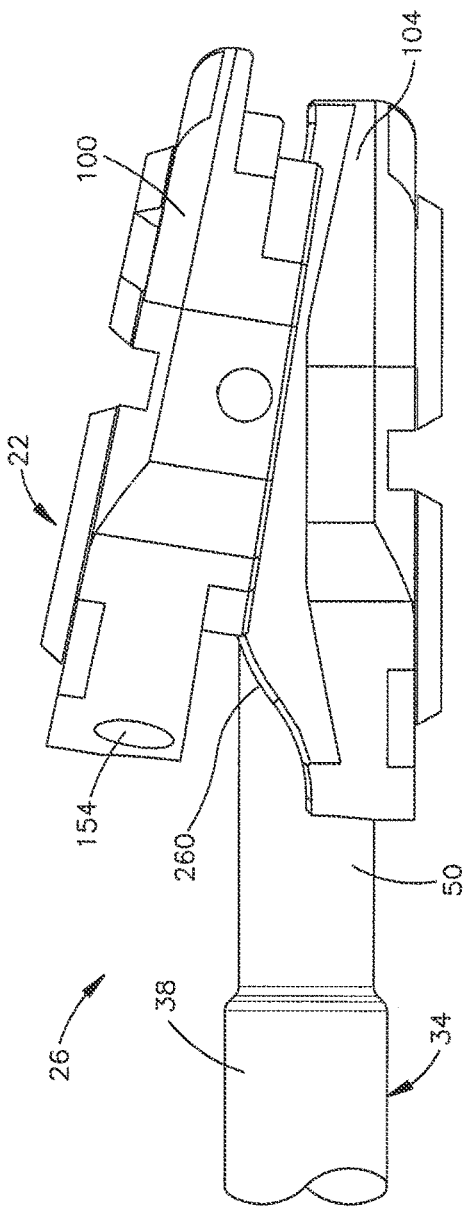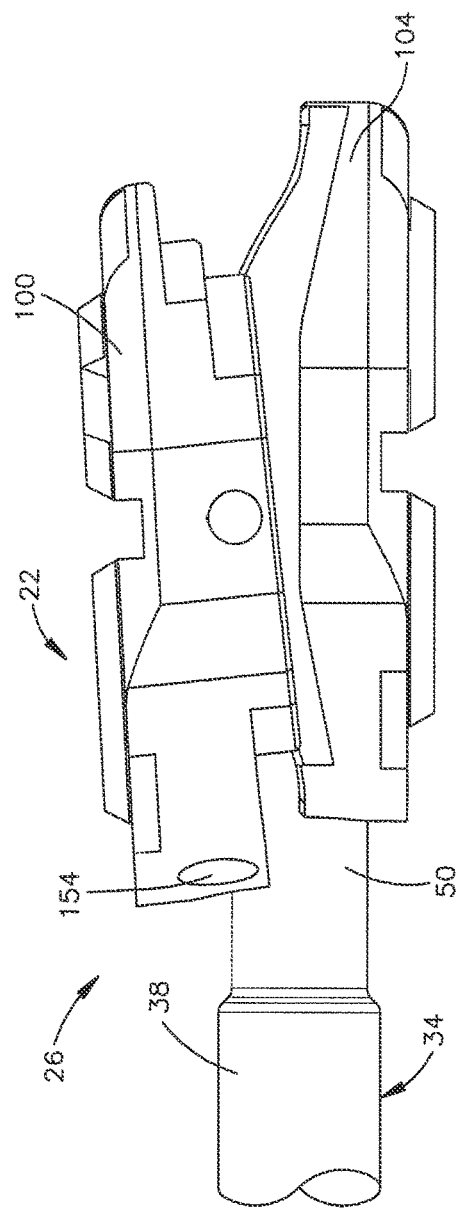

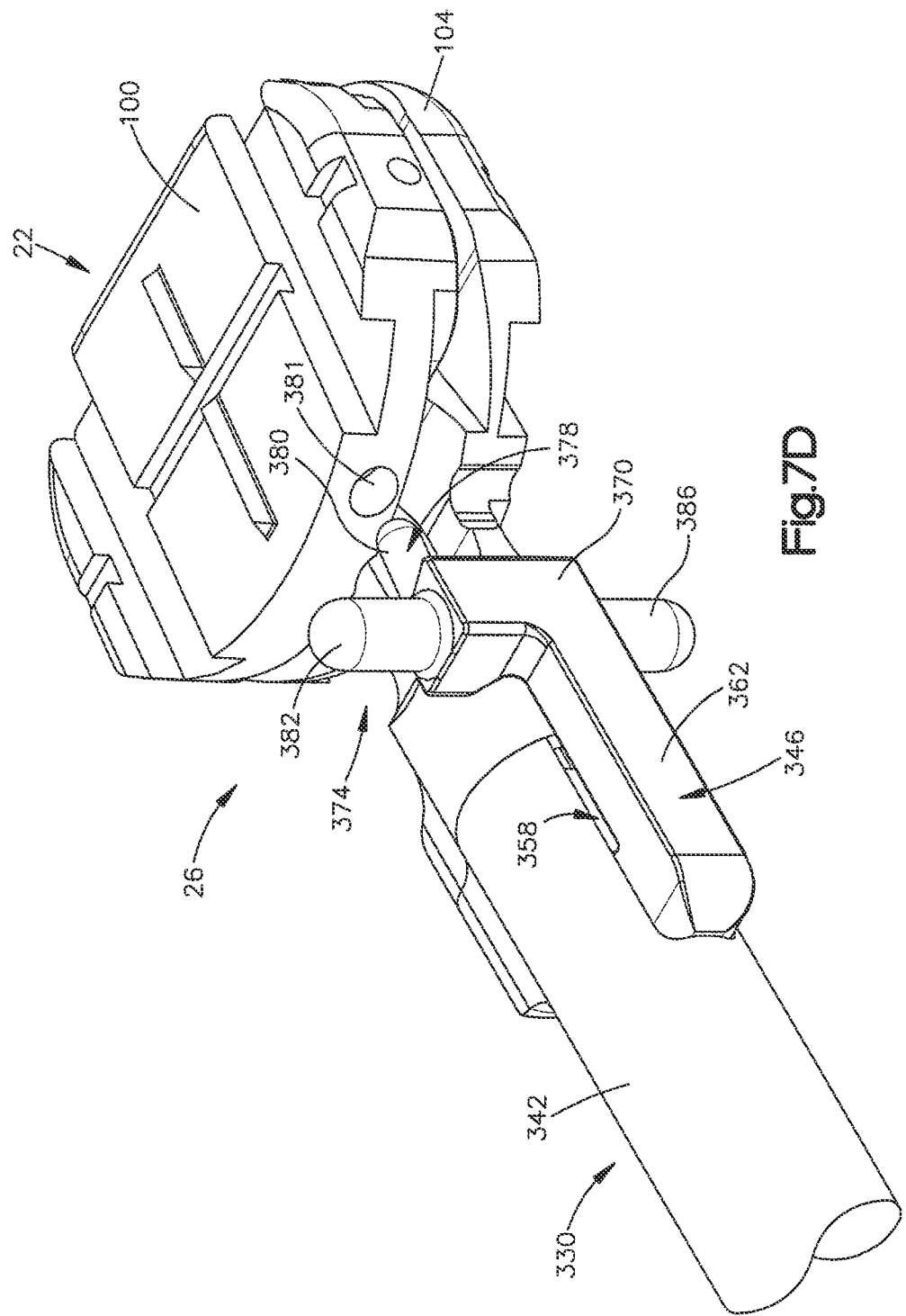

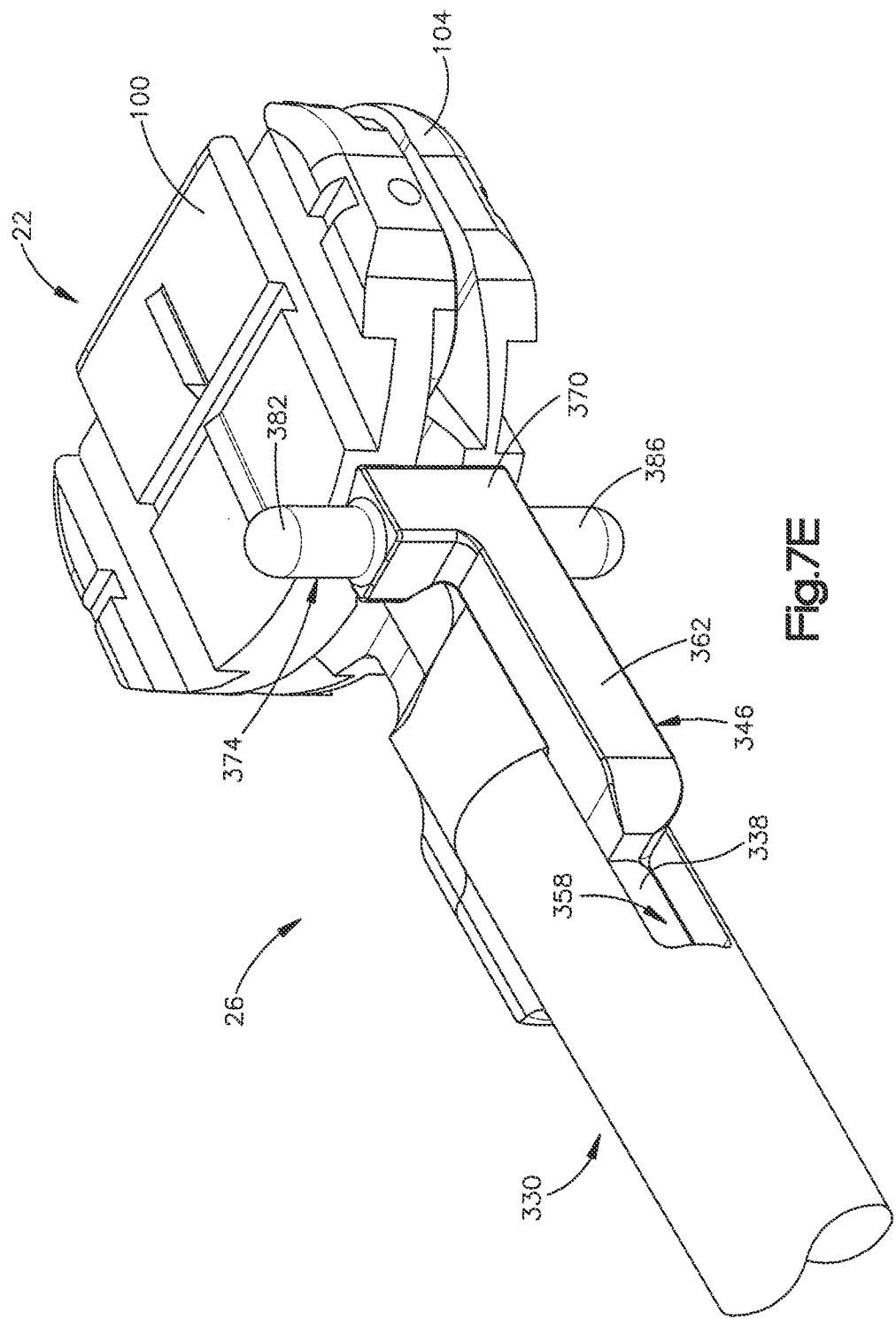

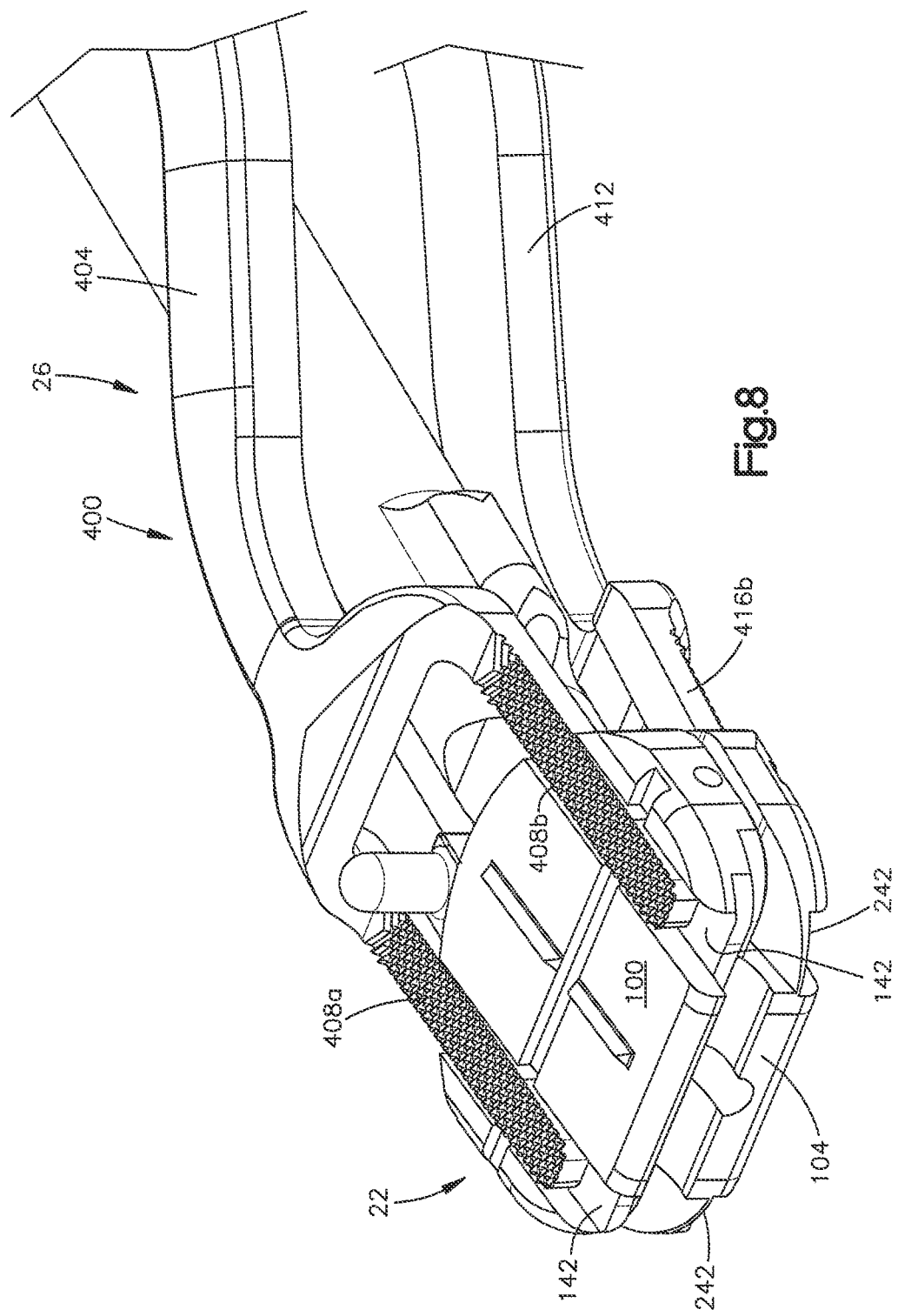

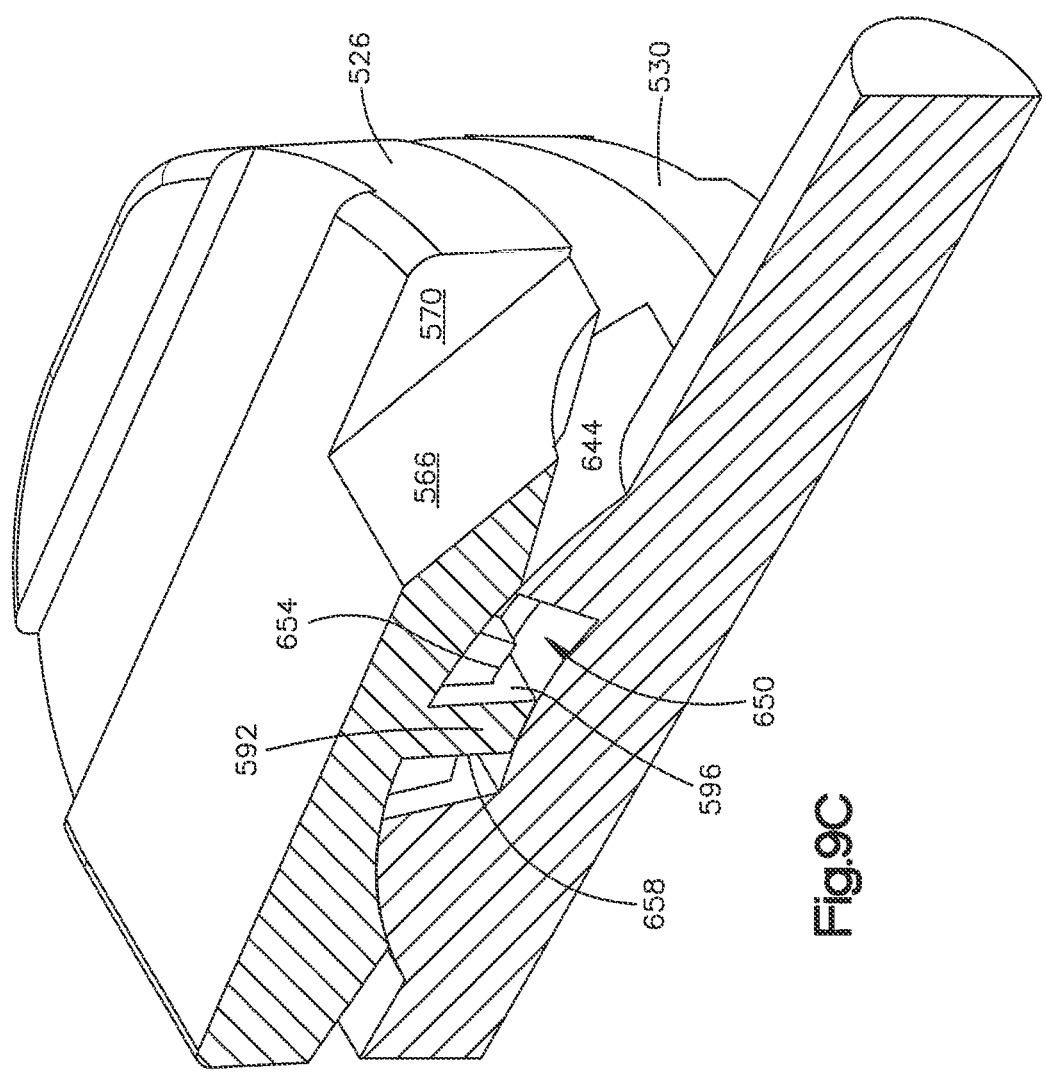

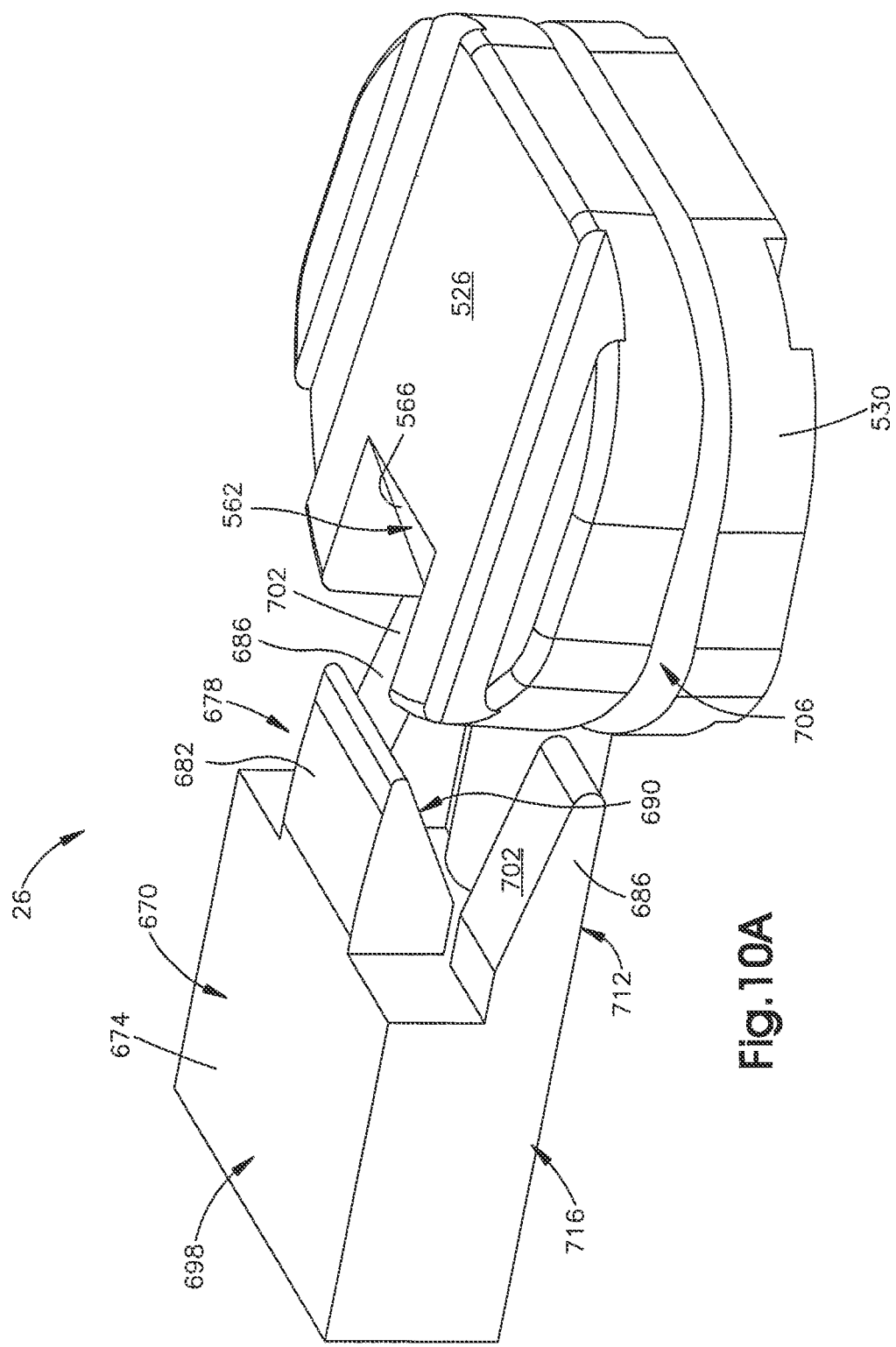

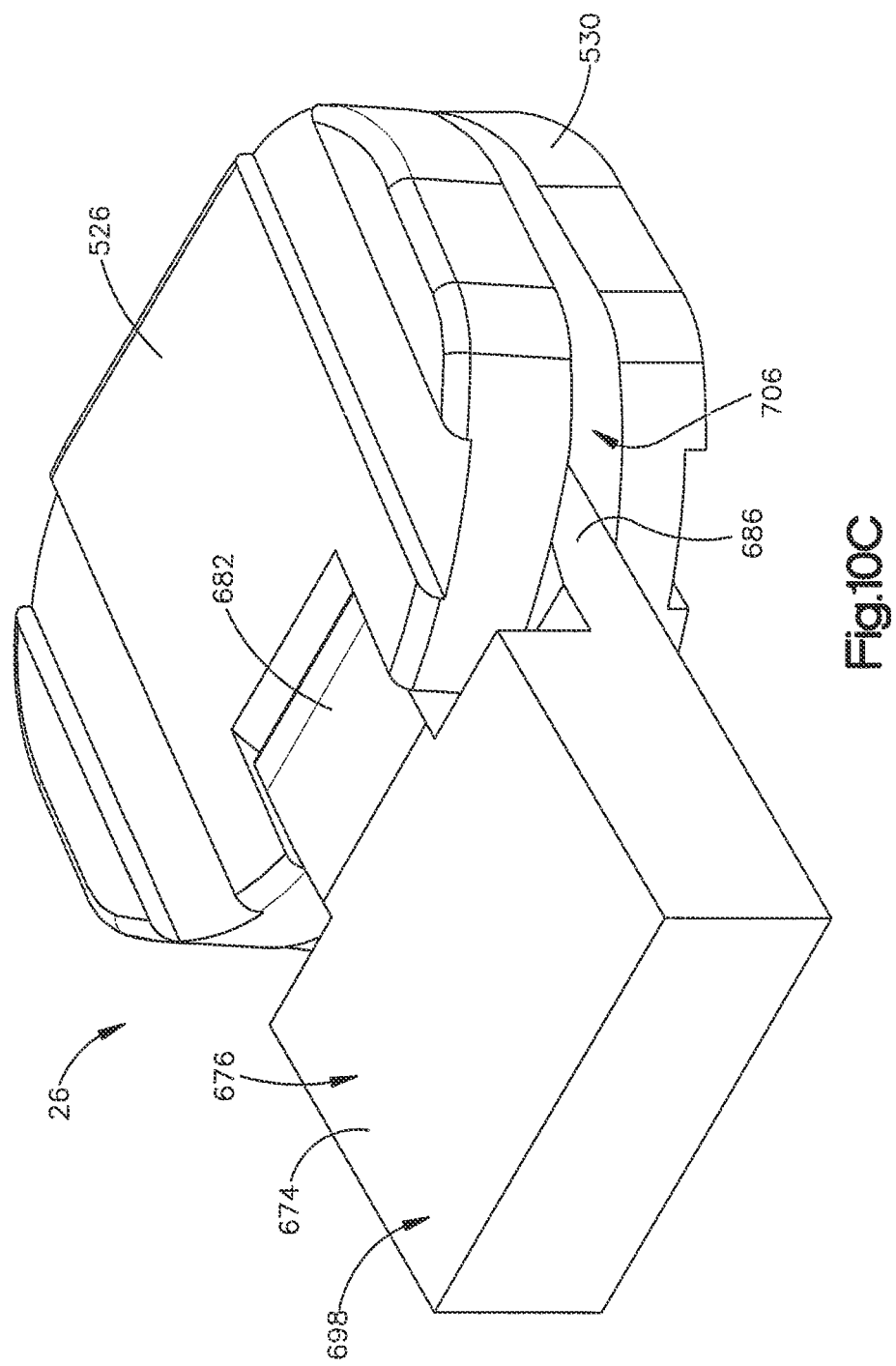

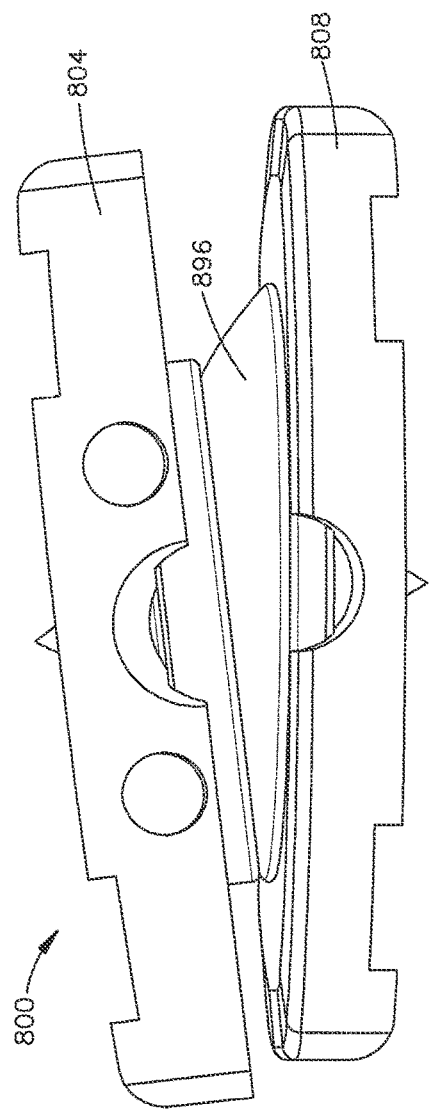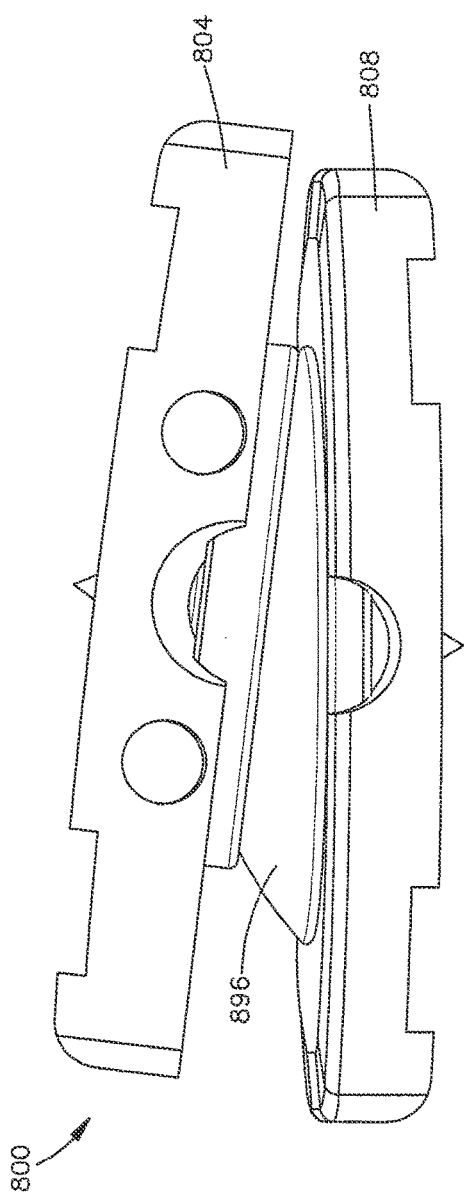
Fig.11B
Fig.11C

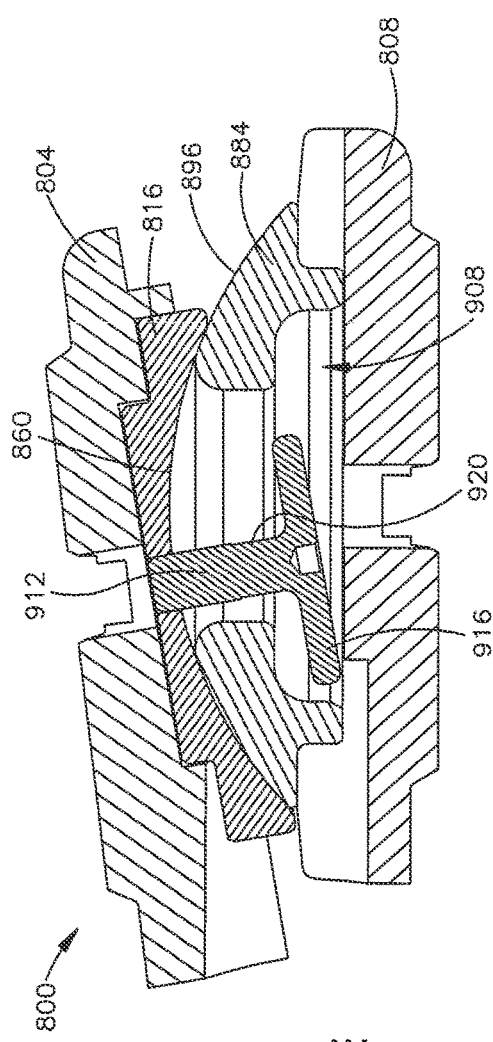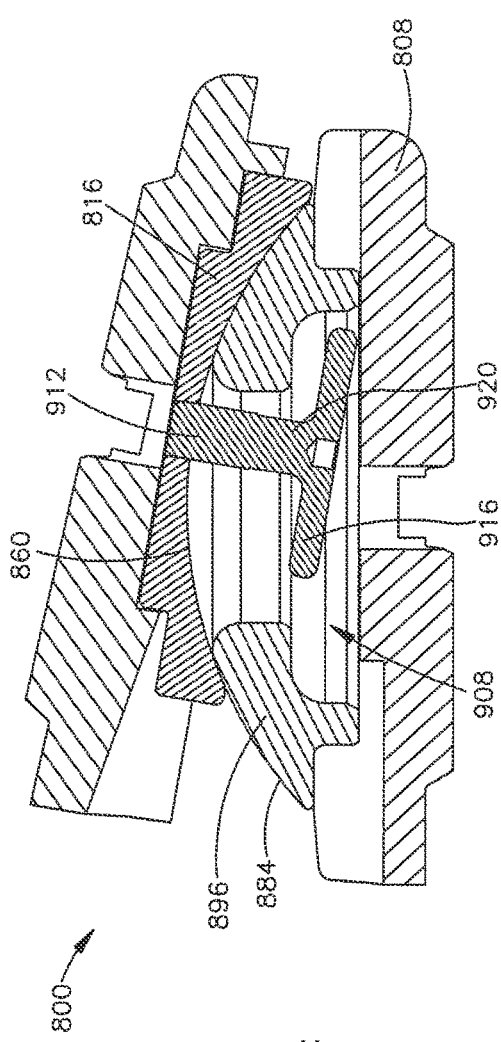

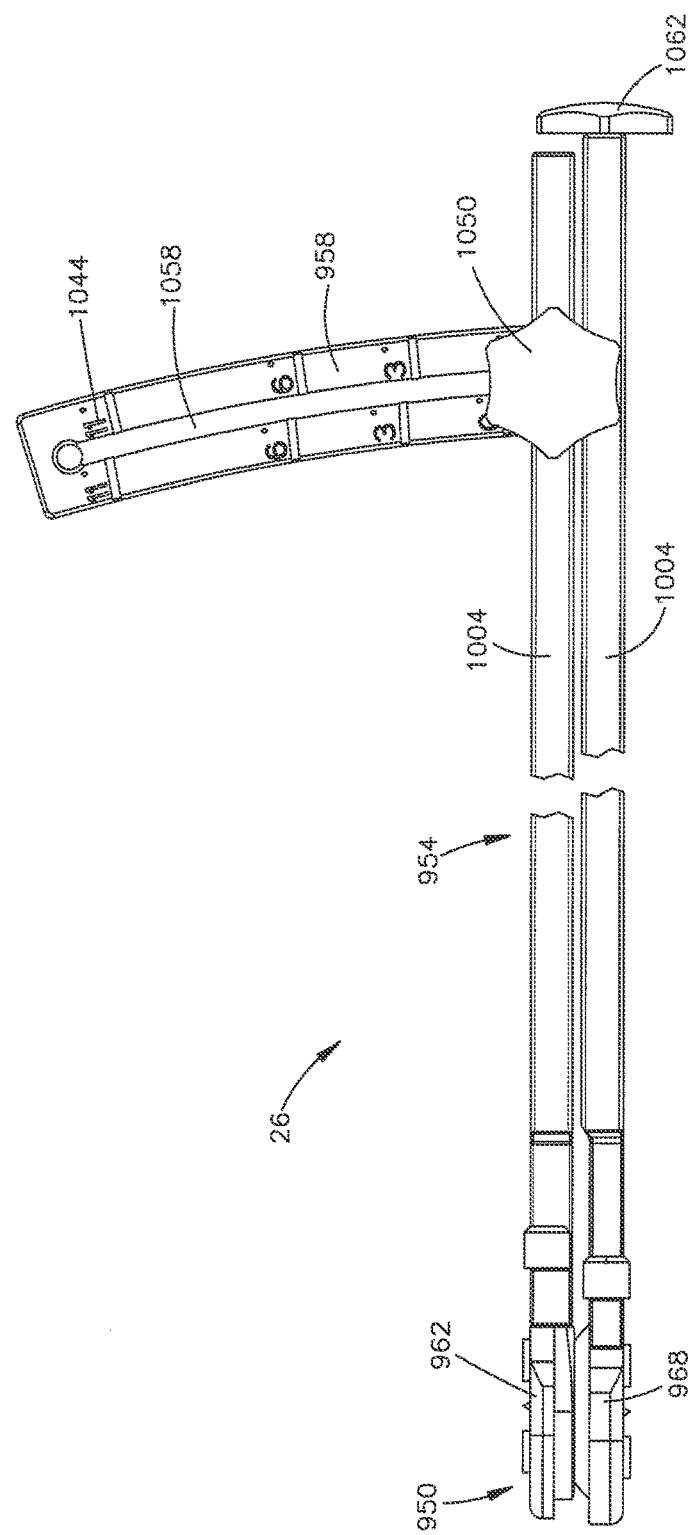

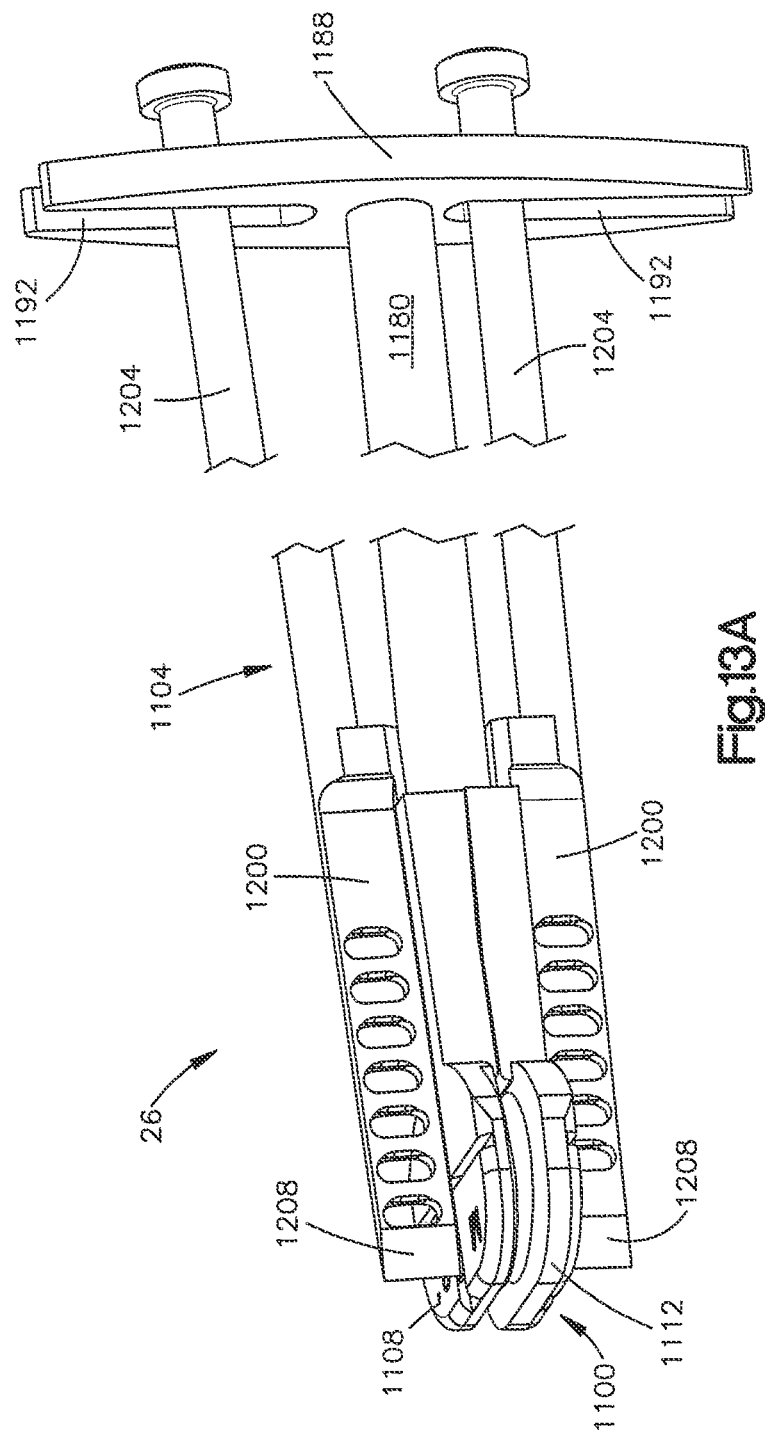

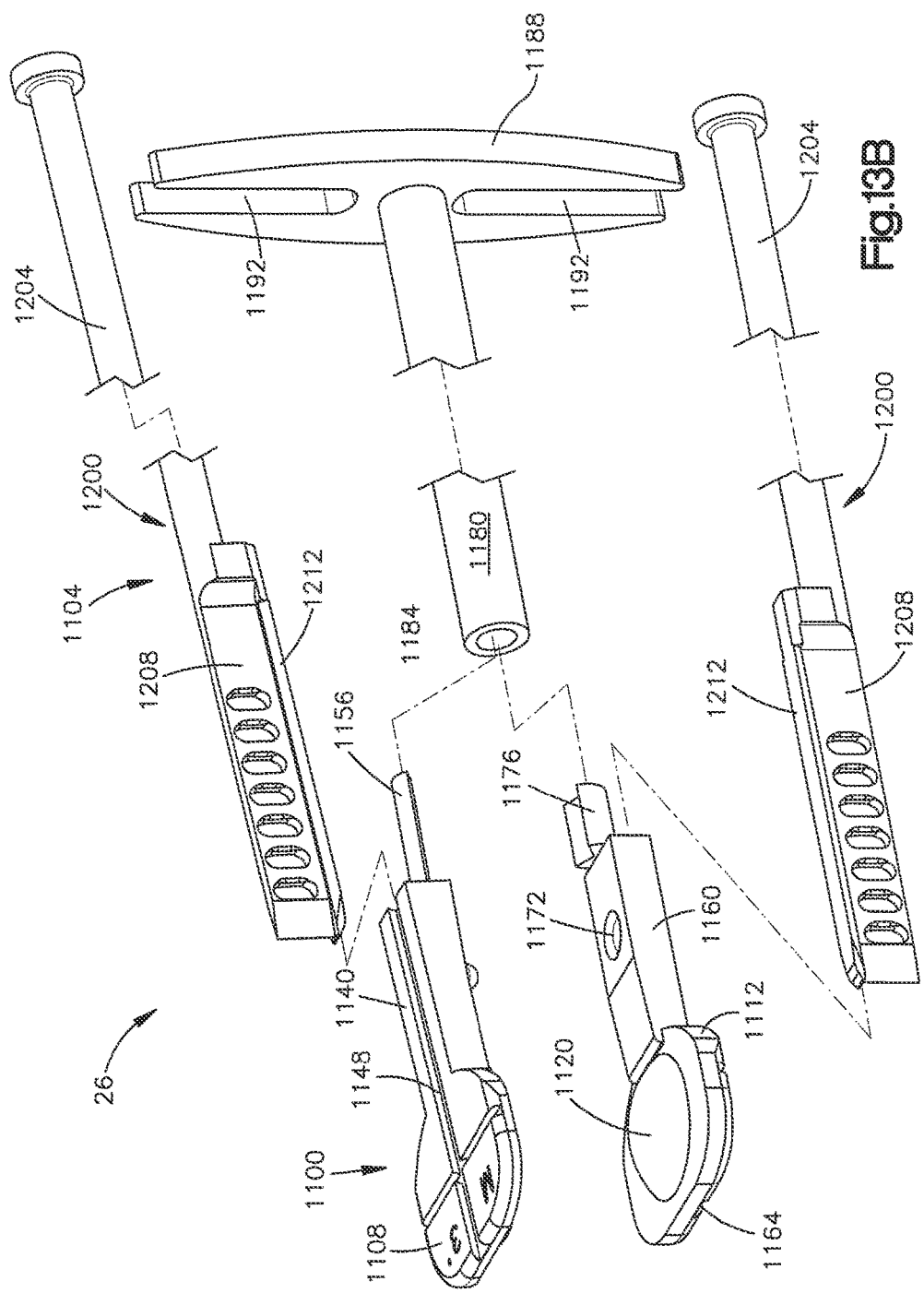

DYNAMIC TRIAL IMPLANTS

CROSS REFERENCE TO RELATED APPLICATIONS

This application is a divisional of U.S. application Ser. No. 12/783,111, filed May 19, 2010 which claims the benefit under 35 U.S.C. § 119(e) to U.S. Provisional Application No. 61/179,566, filed on May 19, 2009, the entireties of each being expressly incorporated herein by reference thereto.

BACKGROUND

Currently, trial implants are inserted into an intervertebral space to accurately gauge the desired size and shape of a permanent intervertebral implant that is to be inserted during a total disc replacement (TDR) surgery. Thus, a plurality of trial implants having varying size and/or shape characteristics are inserted into the intervertebral space until the appropriate size and shape has been determined. Once a trial insert achieves a proper fit, it is then and the permanent implant is inserted having size and shape characteristics that match the properly fitted trial implant. The permanent implant remains installed in the intervertebral space after the surgery has been completed. Conventional trial implants are monobloc, or formed from a single piece of material, and are similar in form to those utilized during an interbody fusion surgery.

SUMMARY

In accordance with one embodiment, a dynamic trial implant system is provided that mimics the articulation of the permanent implant intended to be implanted so as to provide a more accurate determination of the preferred implant size and shape.

Such a trial implant system may include a trial implant that is configured to be temporarily inserted into an intervertebral space defined by a superior vertebral body and an inferior vertebral body. The trial implant may include a superior plate and an inferior plate coupled to the superior plate. The superior plate may have a first mating portion that defines a first articulating interface and the inferior plate may have a second mating portion that defines a second articulating interface. The second articulating interface may be configured to interact with the first articulating interface of the superior plate such that at least one of the superior plate and the inferior plate is capable of movement relative to the other. The first and second articulating interfaces may be primary or auxiliary articulating interfaces. For example, the first and second articulating interfaces may be corresponding curved surfaces or they may be corresponding engagement features.

The trial implant system may also include an inserter instrument. The inserter instrument may include a shaft and a locking block that is translatable along the shaft. The locking block may include a locking mechanism that is configured to engage a locking mechanism defined by the trial implant to thereby restrict movement of the superior plate of the trial implant relative to the inferior plate. When the locking mechanism of the locking block is disengaged from the locking mechanism of the trial implant, the superior plate will be able to move relative to the inferior plate.

BRIEF DESCRIPTION OF THE DRAWINGS

The foregoing summary, as well as the following detailed description of example embodiments of the invention, will be better understood when read in conjunction with the appended drawings. For the purposes of illustrating the trial implant assembly of the present application, there is shown in the drawings example embodiments. It should be understood, however, that the application is not limited to the precise arrangements and instrumentalities shown. In the drawings:

FIG. 1 is a side perspective view of a pair of vertebral bodies separated by an intervertebral space;

FIG. 2A is a side perspective view of a trial implant system including an inserter instrument having a handle, a shaft and a locking block, and a trial implant having a superior plate coupled to an inferior plate in accordance with one embodiment;

FIG. 2B is a detailed perspective view of a distal portion of the trial implant system shown in FIG. 2A;

FIG. 2C is a side perspective view of the trial implant system shown in FIG. 2A with the locking block of the inserter instrument removed for clarity;

FIG. 2D is a side perspective view of the trial implant system shown in FIG. 2A with the inserter instrument decoupled from the trial implant;

FIG. 3A is a top perspective view of the superior plate of the trial implant shown in FIGS. 2A-2D;

FIG. 3B is a bottom perspective view of the superior plate shown in FIG. 3A;

FIG. 4A is a top perspective view of the inferior plate of the trial implant shown in FIG. 2A-2D;

FIG. 4B is a bottom perspective view of the inferior plate shown in FIG. 4A;

FIG. 5B is a side perspective view of the trial implant system shown in FIG. 5A with the locking block of the insert instrument translated along the shaft and engaging the superior plate to thereby restrict movement of the superior plate relative to the inferior plate;

FIG. 6A is a perspective view of the trial implant system shown in FIG. 5B with the locking block removed;

FIG. 6B is a side elevation view of the trial implant system shown in FIG. 6A with the superior plate in a first moved position relative to the inferior plate;

FIG. 6C is a side elevation view of the trial implant system shown in FIG. 6A with the superior plate in a second moved position relative to the inferior plate;

FIG. 7D is a perspective view of the trial implant system shown in FIG. 7A with the locking block disengaged from the superior plate;

FIG. 7E is a perspective view of the trial implant system shown in FIG. 7D with the locking block engaging the superior plate to thereby restrict movement of the superior plate relative to the inferior plate;

FIG. 8 is a perspective view of the trial implant system shown in FIG. 7E with a distractor disposed about the trial implant;

FIG. 9C is a cut-away perspective view of the trial implant shown in FIG. 9A, with the superior plate coupled to the inferior plate;

FIG. 10A is a perspective view of a trial implant system including a locking block and the trial implant shown in FIGS. 9A-9C, in accordance with another embodiment, with the locking block disengaged from the trial implant;

FIG. 10C is another perspective view of the trial implant system shown in FIG. 10B, with the locking block engaging the trial implant;

FIG. 11B is a side elevation view of the trial implant shown in FIG. 11A with the superior plate moved into a first position relative to the inferior plate;

FIG. 11C is a side view of the trial implant shown in FIG. 11A with the superior plate moved into a second position relative to the inferior plate;

FIG. 11E is a sectional side elevation view of the trial implant shown in FIG. 11C;

FIG. 11F is a sectional side elevation view of the trial implant shown in FIG. 11D;

FIG. 12A is a side elevation view of a trial implant system including a measuring member in accordance with another embodiment;

FIG. 13A is a side perspective view of a trial implant system including a trial implant, an inserter instrument, and a pair of chisels in accordance with another embodiment;

FIG. 13B is an exploded assembly view of the trial implant system shown in FIG. 13A.

DETAILED DESCRIPTION

Figure 5A:
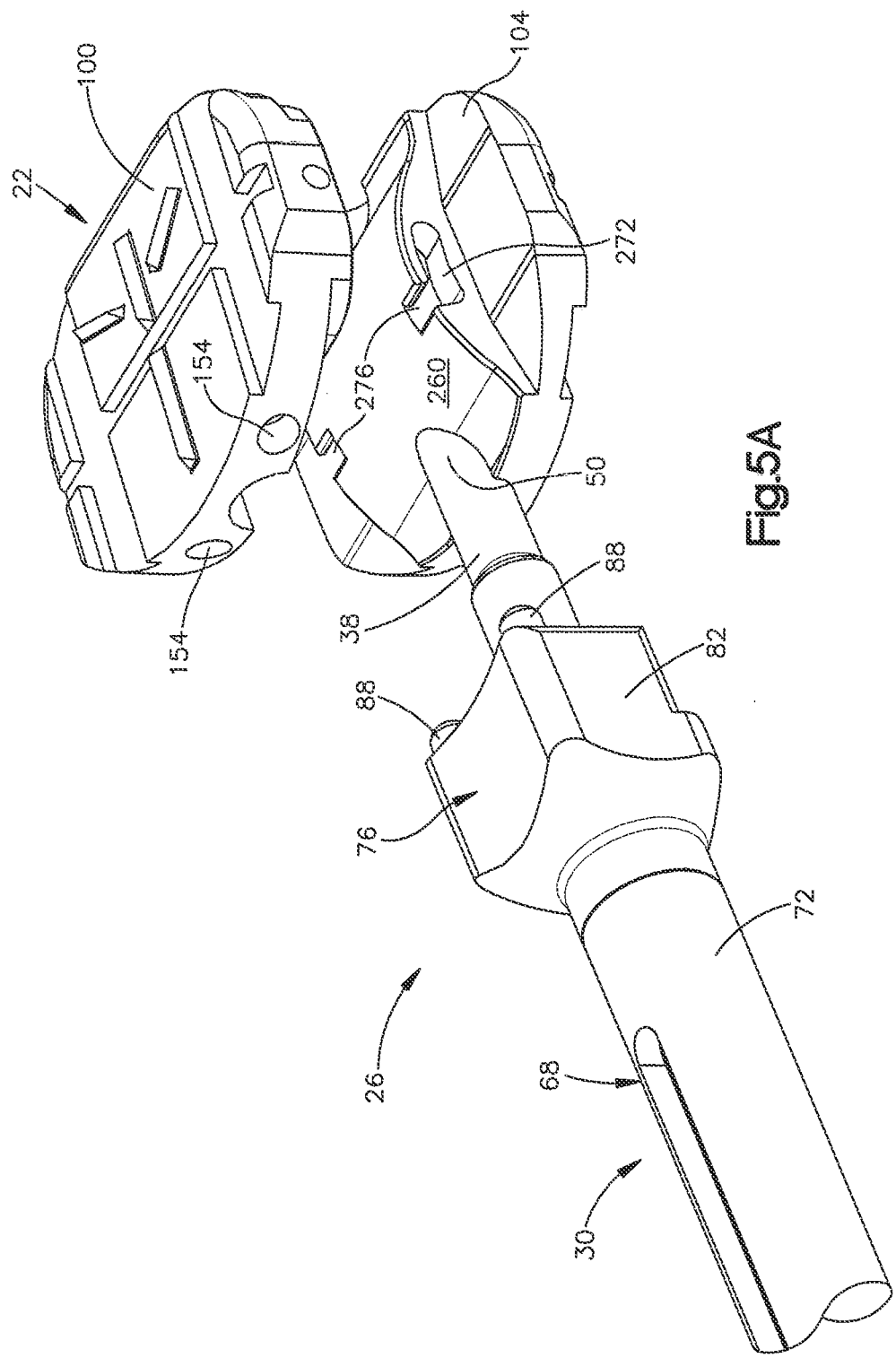
FIG. 5A is a side perspective view of the trial implant system shown in FIG. 2D showing the superior plate decoupled from the inferior plate.

Referring to FIG. 1, a superior vertebral body 10a defines a superior vertebral surface 14a of an intervertebral space 18, and an adjacent inferior vertebral body 10b defines an inferior vertebral surface 14b of the intervertebral space 18. Thus, the intervertebral space 18 is disposed between the vertebral bodies 10a-b. The vertebral bodies 10a-b can be anatomically adjacent vertebral bodies, or can remain after a vertebral body has been removed from a location between the vertebral bodies 10a-b. As illustrated, the intervertebral space 18 is illustrated after a discectomy, whereby the disc material has been removed or at least partially removed to prepare the intervertebral space 18 to receive a disc implant that can achieve height restoration. Prior to inserting the permanent disc implant in the inteverebral space, one or more temporary trial implants of various dimensions, such as a movable/dynamic trial implant 22 of a trial implant system 26 illustrated in FIGS. 2A-2D, are inserted into the intervertebral space 18 to determine the optimal size and geometry of the actual disc implant to be permanently inserted. The implant 22 is configured such that a surgeon will be able to find the best permanent implant that matches with the intervertabral space 18 morphology. The intervertebral space 18 can be disposed anywhere along the spine as desired, including at the lumbar, thoracic, and cervical regions of the spine.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

The trial implant system 26 is described herein as extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the trial implant 22 is implanted into an intervertebral space, such as the intervertebral space 18, the transverse direction T extends vertically generally along the superior-inferior (or caudal-cranial) direction, while the horizontal plane defined by the longitudinal direction L and lateral direction A lies generally in the anatomical plane defined by the anterior-posterior direction, and the medial-lateral direction. Accordingly, the directional terms "vertical" and "horizontal" are used to describe the implant system 26 and its components as illustrated merely for the purposes of clarity and illustration.

Referring now also to FIGS. 2A-2D, a trial implant system 26 is configured to be temporarily positioned within an at least partially cleared out disc space, such as the disc space 18 disposed between the superior vertebral body 10a and the inferior vertebral body 10b. The trial implant system 26 includes a trial implant 22 coupled to an inserter instrument 30. The inserter instrument 30 can be formed from any desired material such as stainless steel, while the trial implant 22 can be formed from any desired material such as a titanium alloy. It should be appreciated that both the inserter instrument 30 and the trial implant 22 can be formed from a range of biocompatible metals or polymers, such as cobalt chromium molybdenum (CoCrMo), titanium and titanium alloys, stainless steel, ceramics, or polymers such as polyetheretherketone (PEEK), polyetherketoneketone (PEKK), and bioresorbable materials.

The inserter instrument 30 includes a shaft 34 having a shaft body 38 that defines a proximal end 42a, and a distal end 42b that is separated from the proximal end 42a along a longitudinally extending central shaft axis S. The shaft 34 includes a handle coupling portion 46 at the proximal end 42a of the shaft body 38, and a trial implant coupling member 50 at the distal end 42b of the shaft body 38. The handle coupling portion 46 may be a hex coupling configured to be received by a corresponding coupling portion of a handle, such as handle 350 shown in FIG. 7A. As shown in FIG. 2D, the coupling member 50 is configured to be coupled to a complementary coupling member 54 of the trial implant 22 so as to connect the shaft 34 and thus the inserter instrument to the trial implant 24. In the illustrated embodiment, the coupling member 50 of the inserter instrument 30 includes external threads (not shown for clarity) disposed proximate to the distal end of the shaft 34 configured to engage threads of the trial implant 22 to thereby couple the inserter instrument 30 to the trial implant.

When the inserter instrument 30 is coupled to the trial implant 22, the proximal end 42a of the shaft body 38 defines a proximal end 62a of the implant system 26, and the trial implant 22 defines an opposed distal end 62b of the implant system 26. Accordingly, a distal spatial relationship is used herein to refer to a longitudinal direction for the proximal end 62a toward the distal end 62b, and a proximal spatial relationship is used herein to refer to a longitudinal direction from the distal end 62b toward the proximal end 62a.

As shown in FIGS. 2A, 2B, and 2D, the inserter instrument 30 also includes a locking block 68 having a tube 72 translatable about an external surface of the shaft body 38, and a head portion 76 extending from a distal end of the tube 72. As shown, the tube 72 and the head portion 76 include a longitudinal bore 80 extending completely therethrough, and the shaft body 38 extends through the bore 80. Thus, the locking block 68 is capable of translating distally and proximally along the shaft body 38. As best shown in FIG. 2D, the head portion 76 includes a head body 82 and a locking mechanism 84 that extends distally from the head body 82 toward the trial implant 22. In the illustrated embodiment, the locking mechanism 84 includes a pair of pins 88 that extend toward the trial implant 22. As shown, the locking mechanism 84 is configured to engage a complementary locking mechanism 92 of the trial implant 22.

As shown in FIG. 2D, the trial implant 22 that is configured to be coupled to the distal end of the inserter instrument 30, includes an upper or superior plate 100, coupled to a lower or inferior plate 104. The superior plate 100 is coupled to the inferior plate 104 such that either the superior plate 100, the inferior plate 104, or both is capable of movement relative to the other. Such movement allows the trial implant 22 to at least partially simulate actual implant movement, and thus provide an image of the final implant on implantation. Furthermore, it should be understood that the trial implant 22 may be provided in a variety of dimensions depending on the individual receiving the implant and the location of the intervertebral space that receives the trial implant.

As shown in FIGS. 3A-3B, the superior plate 100 of the trial implant 22, includes a generally oval shaped body 110 having a first mating portion 114 incorporated into a bottom or inferior side of the body 110. As shown, the body 110 defines an upper or superior, or outer transverse engagement surface 118 configured to contact the inferior endplate of the superior vertebral body 10a, a curved proximal surface 122 and a curved distal surface 126. While the superior surface 118 is generally flat, the superior surface 118 includes medial stabilizers 130, and lateral stabilizers 134 that serve to prevent the trial implant 22 from slipping or becoming displaced within the disc space during and subsequent to insertion. As shown, the medial stabilizers 130 are disposed along the longitudinal direction and the lateral stabilizers 134 are disposed along the lateral direction. Alternatively or in addition thereto, teeth or other surface texturing can extend up from the superior surface 118 to prevent displacement of the trial implant 22. The superior surface 118 further includes a pair of spaced apart rails or grooves 142 disposed along the longitudinal direction for receiving upper arms of a distractor instrument, such as the upper arms of the distractor instrument 400 shown in FIG. 10.

As shown in FIGS. 3A-3B, the proximal surface 122 of the body 110 defines a locking mechanism 92 of the trial implant 22 that is configured to engage the locking mechanism 84 defined by the inserter instrument 30 to thereby restrict movement of the superior plate 100 relative to the inferior plate 104. As shown, the locking mechanism 92 includes two bores or holes 154 extending into the proximal surface 122 of the superior plate 100. Thus, each pin 88 of the inserter instrument's locking mechanism 84, is configured to be received by a respective bore 154 of the trial implant's locking mechanism 92. Furthermore, a partial bore 158 extends into the proximal surface 122 of the superior plate 100 between the bores 154. The partial bore 158 provides clearance for the shaft 34 of the inserter instrument 30 when the inserter instrument is attached to the trial implant 22.

As shown in FIG. 3B, the first mating portion 114 defines a primary articulation interface such as an inferior articulating surface 160 and an auxiliary articulation interface such as an engagement feature 164 for coupling the superior plate 100 to the inferior plate 104. The inferior surface 160 is curved along the longitudinal direction and is concave. Because the inferior surface 160 is concave, the first mating portion 114 also defines two opposing side surfaces 168. As shown in FIG. 3B, the engagement feature 164 is incorporated into the side surfaces 168. In particular, the engagement feature 164 includes a pin 172 that extends laterally out from each respective side surface 168. As shown, the pins 172 are located proximate to the longitudinal center of each side surface 168.

As shown in FIGS. 4A-4B, the inferior plate 104, includes a generally oval shaped body 210 having a second mating portion 214 incorporated into a top or superior side of the body 210. As shown, the body 210 defines a lower or inferior, or outer transverse engagement surface 218 configured to contact the superior endplate of the inferior vertebral body 10b, a curved proximal surface 222 and a curved distal surface 226. While the inferior surface 218 is generally flat, the inferior surface 218 includes medial stabilizers 230, and lateral stabilizers 234 that serve to prevent the trial implant 22 from slipping or becoming displaced within the disc space during and subsequent to insertion. As shown, the medial stabilizers 230 are disposed along the longitudinal direction and the lateral stabilizers 234 are disposed along the lateral direction. Alternatively or in addition thereto, teeth or other surface texturing can be included to prevent displacement of the trial implant 22. The inferior surface 218 further includes a pair of spaced apart rails or grooves 242 disposed along the longitudinal direction for receiving lower arms of a distractor instrument, such as the lower arms of the distractor instrument 400 (shown in FIG. 10).

As shown in FIGS. 4A-4B, the proximal surface 222 of the body 210 defines the coupling member 54 of the trial implant 22 that is configured to couple the trial implant 22 to the inserter instrument 30. As shown, coupling member 54 includes a bore 246 that extends longitudinally into the proximal surface 222 of the inferior plate 100. The bore 246 is sized to receive the external threads of the shaft 34. Thus, the bore 246 includes internal threads disposed about the periphery of the bore 246 that are configured to mate with the external threads of the shaft 34 so as to couple the inserter instrument 30 to the trial implant 22.

As shown in FIG. 4A, the second mating portion 214 defines a primary articulation interface, such as a superior articulating surface 260 and an auxiliary articulation interface, such as an engagement feature 264 for coupling the inferior plate 104 to the superior plate 100. The superior surface 260 is curved along the longitudinal direction and is convex. Because the superior surface 260 is convex, the second mating portion 214 also defines two outer side surfaces 268. As shown in FIG. 4B, the engagement feature 264 is defined in the side surfaces 268. In particular, the engagement feature 264 includes a slot 272 that extends laterally into each respective side surface 268. Each slot 272 also extends in the longitudinal direction and follows an arch that is similar to the arch of the curved superior surface 260. Proximate to the proximal end of each slot 272 is an opening 276 that extends down through the superior surface 260 and into a respective slot 272. As shown, the slots 272 are located proximate to the longitudinal center of each side surface 268.

As shown in FIG. 5A, the inserter instrument 30 is coupled to the trial implant 22 by threaded engagement of the threaded coupling member 50 of the inserter instrument shaft 34 with the threaded engagement member 54 defined by the inferior plate 104 of the trial implant 22. As shown, the superior plate 100 may be coupled to the inferior plate 104, once the inserter instrument 30 is secured to the inferior plate 104. This is accomplished by lowering the superior plate 100 onto the inferior plate 104 such that the pins 172 of the superior plate 100 enter through respective openings 276 and into the slots 272 of the inferior plate 104. Because of the engagement between the pins 172 and the slots 272 the superior plate 100 will be able to move relative to the inferior plate 104.

As shown in FIG. 5B, the movement of the superior plate 100 relative to the inferior plate 104 may be restricted by advancing the locking block 68 distally until the pins 88 of the locking block 68 engage the bores 154 of the superior plate 100. Once the movement of the superior plate 100 is restricted, the inserter instrument 30 may insert the trial implant into the intervertebral space 18.

As shown in FIGS. 6A-6C, the locking block 68 may be translated proximally until the pins 88 are completely removed from the bores 154 of the superior plate 100. Once removed, the superior plate 100 will be able to move relative to the inferior plate 104. For example, the superior plate 100 may be moved to a first position as shown in FIG. 6B in which the superior plate 100 is moved distally about the inferior plate 104. In particular, the pin 172 of the superior plate 100 slides distally within the slot 272 of the inferior plate 104, while the inferior surface 160 of the superior plate 100 slides along the superior surface 260 of the inferior plate. The curved inferior and superior surfaces 160, 260, allow the superior plate 100 to move distally along an arc in the longitudinal direction.

Similarly, the superior plate 100 may be moved to a second position as shown in FIG. 6C in which the superior plate 100 is moved proximally about the inferior plate 104. In particular, the pin 172 of the superior plate 100 slides proximally within the slot 272 of the inferior plate 104, while the inferior surface 160 of the superior plate 100 slides along the superior surface 260 of the inferior plate. The curved inferior and superior surfaces 160, 260, allow the superior plate 100 to move proximally along an arc in the longitudinal direction. As shown, because the curved inferior and superior surfaces 160, 260 are arced only in the longitudinal direction, movement of the superior plate is restricted to the longitudinal direction.

Figure 7A:
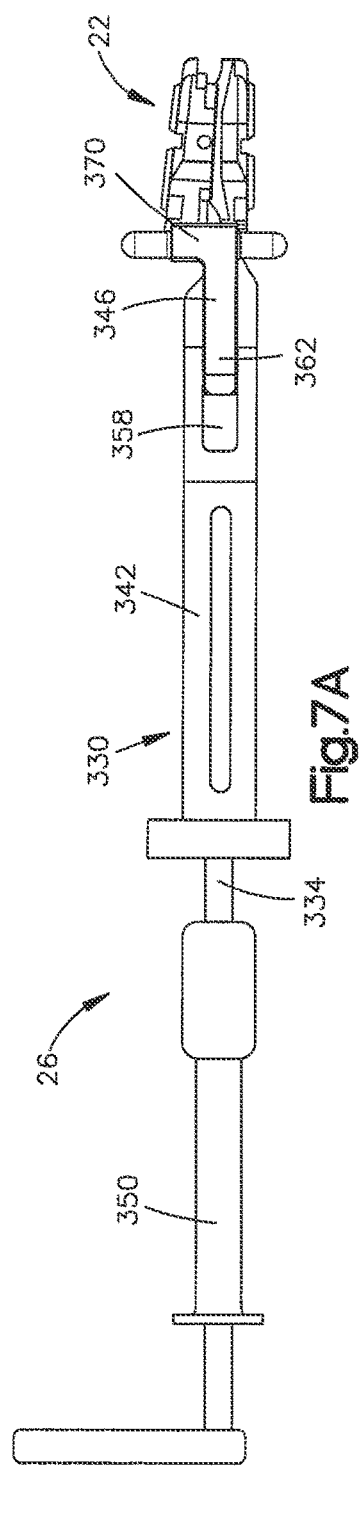
FIG. 7A is a side elevation view of a trial implant system including an inserter instrument having a handle, a shaft and a locking block, and a trial implant having a superior plate coupled to an inferior plate in accordance with another embodiment.
Figure 7B:
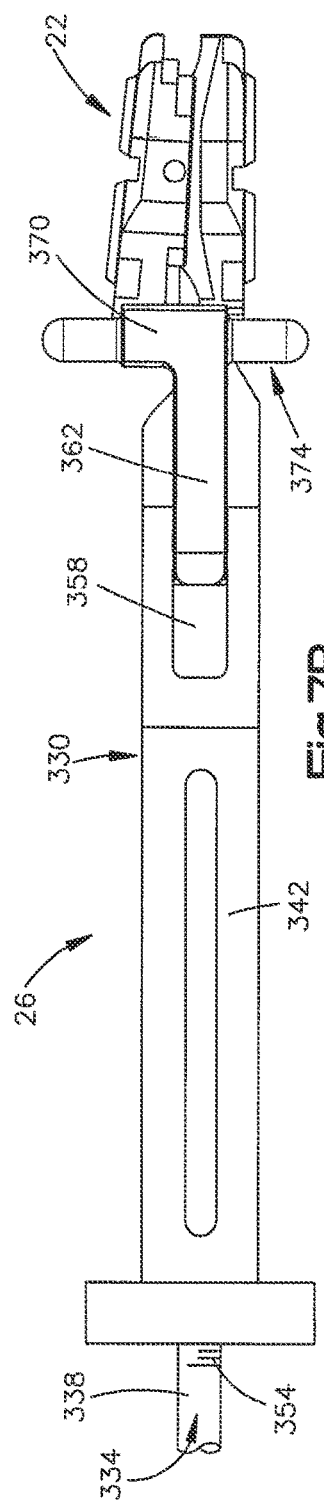
FIG. 7B is a detailed side view of the trial implant system shown in FIG. 7A with the handle of the inserter instrument removed for clarity.
Figure 7C:
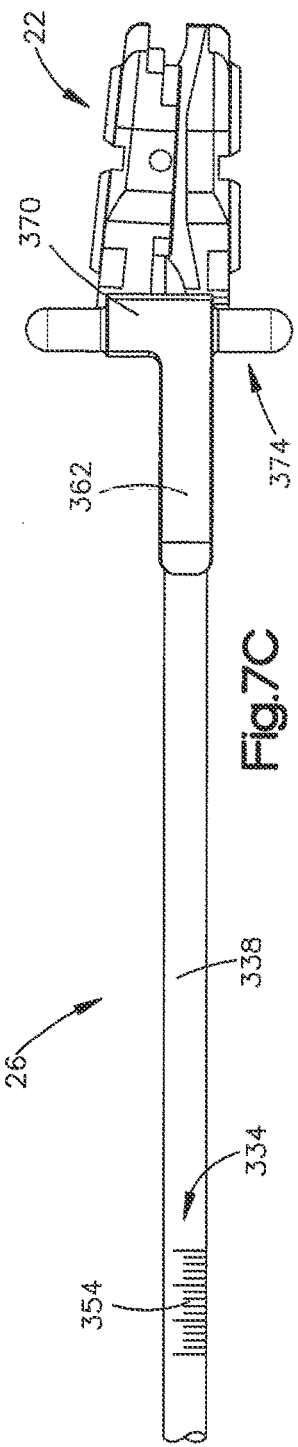
FIG. 7C is a side view of the trial implant system shown in FIG. 7B with the locking block of the inserter instrument removed for clarity.

As shown in FIGS. 7A-7E, the trial implant system 26 may include an inserter instrument constructed to include a stop member. As shown in FIGS. 7A-7C, an inserter instrument 330 includes a shaft 334 having a shaft body 338, a sleeve 342 translatable about the shaft body 338, and a locking block 346 coupled proximate to a distal end of the shaft body 338. The instrument 330 also includes a stop member 346 attached to the locking block 346. The inserter instrument 330 is configured to not only insert the trial implant 22 but is also configured to measure the depth of the inserted trial implant 22.

As shown in FIGS. 7A-7C, the shaft body 338 is elongate in the longitudinal direction and includes a distal end that is configured to couple the inserter instrument 330 to the trial implant 22, and a proximal end that is configured to couple the inserter instrument 330 to a handle 350. Though not shown, the distal and proximal ends of the shaft body 338 may be similar to those described in reference to shaft body 38. Therefore, the distal end of shaft body 338 may include external threads and the proximal end of shaft body 338 may include a hex. As shown in FIG. 7C, the shaft body 338 further includes indicia marks 354 near its proximal end. The indicia marks 354 provide measurements for a user to determine the depth of the inserted trial implant 22.

As shown in FIGS. 7A and 7B, the sleeve 342 is disposed about the shaft body 338 such that the shaft body 338 is capable of translating within the sleeve 342. As shown, the sleeve 342 includes a pair of opposing slots 358 proximate to its distal end. The slots 358 extend laterally completely through the sleeve 342, and along the sleeve 342 in the longitudinal direction.

As shown in FIGS. 7C, 7D and 7E, the locking block 346 is attached to the shaft body 338 proximate to a distal end of the shaft body 338. In particular, the locking block 346 includes an arm 362 that extends out laterally from the shaft body 338 and then distally in the longitudinal direction. As shown, the arm 362 extends through the slot 358 defined by the sleeve 342. Because the arm 362 extends through the slot 358, the locking block 346 will be capable of moving with the shaft 330 relative to the sleeve 342 as the shaft 330 is translated distally or proximally. Furthermore, the slot 358 will prevent the locking block 346 from rotating as the shaft 330 is translated distally or proximally. This is because the transverse height of the arm 362 is substantially equal to the transverse height of the slot 358.

As shown in FIG. 7D, the locking block 346 further includes a head portion 370 at the distal end of the arm 362. As shown, a stop member 374 extends in the transverse direction from the head portion 370 and a locking mechanism 378 extends distally from a distal face of the head portion 370, as shown in FIG. 7D.

The locking mechanism 378 includes a pin 380 that is configured to engage a locking mechanism of the trial implant 22, such as a bore 381 defined in the superior plate 100 of the trial implant 22. As shown in FIGS. 7D and 7E, the pin 380 is configured to engage the bore 381. When the pin 380 is engaged with the bore 381 of the superior plate 100, as shown in FIG. 7E, the superior plate 100 is restricted from moving relative to the inferior plate 104 and the trial implant 22 may be implanted into the intervertebral space 18. Alternatively when the shaft 334 is translated proximally, the pin 380 will disengage from the bore 381, and the superior plate 100 will be able to move relative to the inferior plate 104.

As shown in FIG. 7D, the stop member 374 includes a first stop 382 that extends up from a top surface of the head portion 370 and a second stop 386 that extends down from a bottom surface of the head portion 370. The stop member 374 and in particular the first stop 382 and second stop 386 extend such that they have an overall height that is greater than the height of the trial implant 22.

In operation, the inserter instrument 330 is coupled to the trial implant 22, such that the pin 380 is engaged with the bore 381, the first stop 382 abuts or otherwise engages the superior plate 100, and the second stop 386 abuts or otherwise engages the inferior plate 104. The trial implant 22 may then be inserted into the intervertebral space 18. By rotating the handle 350 counter clockwise the shaft 330 will unscrew from the inferior plate 104 and move the first and second stops 382, 386 proximally away from the trial implant 22. This will allow the trial implant 22 to be inserted deeper into the intervertebral space 18. When the appropriate depth has been achieved, the locking block 346 is moved distally, and reengages the trial implant 22. That is, the pin 380 reengages the bore 381, the first stop 382 reengages the superior plate 100, and the second stop 386 reengages the inferior plate 104. The depth of the trial implant 22 may then be measured using the indicia 354 on the shaft body 338.

As shown in FIG. 8, the trial implant system 26 may also include a distractor instrument 400 for separating the superior and inferior vertebras 10a and 10b. As shown, the distractor 400 includes an upper arm 404 that terminates distally in a pair of upper fork arms 408a, 408b, and a lower arm 412 that terminates distally in a pair of lower fork arms 416a, 416b. The upper fork arms 408a, 408b are configured to slidingly engage the grooves 142 of the superior plate 100, and the lower fork arms 416a, 416b are configured to slidingly engage the grooves 242 of the inferior plate 104, during the insertion of the coupled superior and inferior plates 100, 104 into the cleared out intervertebral disc space 18. The distractor instrument 400 creates, via the pivoting of the upper and inferior arms 404 and 412, and maintains the distraction of the cleared out space 18 while allowing the trial implant 22 to be guided along the fork arms 408a, 408b, 416a, and 416b.

The trial implant system 26 may include other trial implants including other features to couple the superior plate to the inferior plate and to restrict movement of the superior plate relative to the inferior plate. For example, as shown in FIGS. 9A-9C, a trial implant 522 includes a superior plate 526 coupled to an inferior plate 530, and is configured to move relative to the inferior plate 530.

Figure 9A:
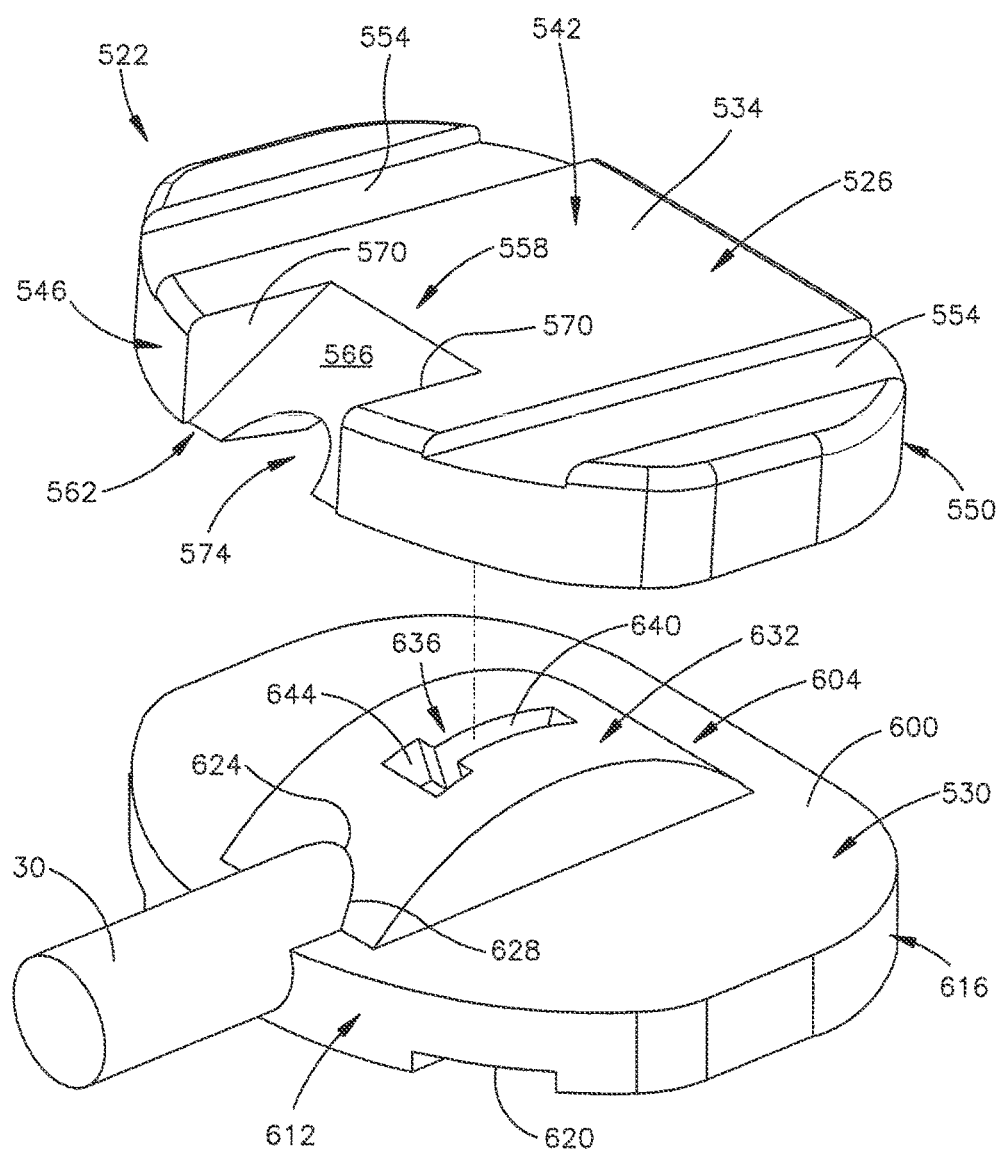
FIG. 9A is a top perspective view of a trial implant system in accordance with another embodiment, showing a superior plate decoupled from an inferior plate.
Figure 9B:
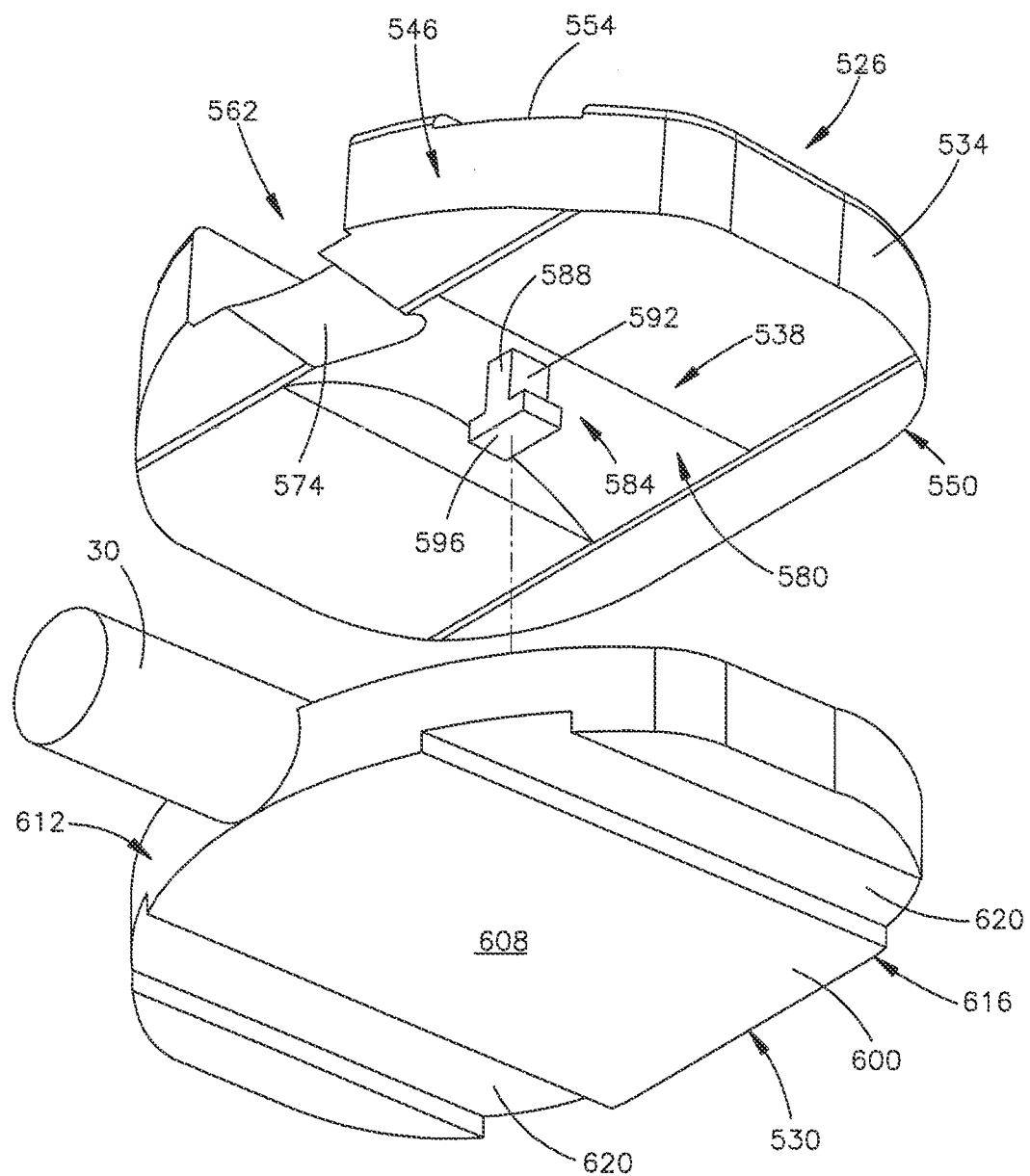
FIG. 9B is a bottom perspective view of the trial implant shown in FIG. 9A.

As shown in FIGS. 9A and 9B, the superior plate 526 includes a generally oval shaped body 534 having a first mating portion 538 incorporated into a bottom or inferior side of the body 534. As shown, the body 534 defines an upper or superior, or outer transverse engagement surface 542 configured to contact the inferior endplate of the superior vertebral body 10a, a proximal surface 546 and a distal surface 550. The superior surface 542 is generally flat and includes a pair of spaced apart rails or grooves 554 disposed along the longitudinal direction for receiving arms of a distractor instrument, such as the distractor instrument 400 shown in FIG. 10.

As shown in FIGS. 9A and 9B, the proximal surface 546 of the body 534 defines a locking mechanism 558 of the trial implant 522 that is configured to engage a locking mechanism defined by an inserter instrument. As shown, the locking mechanism 558 includes an angled recess 562 extending from a generally bottom portion of the proximal surface 546 and through to the superior surface 542 of the superior plate 100. As shown the recess 562 is defined by an angled bottom surface 566 and opposing side surfaces 570. The recess is configured to receive a locking mechanism defined by the inserter instrument. Furthermore, a partial bore 574 extends into the angled surface 566 of the superior plate 100 to provide clearance for a shaft, such as shaft 34 of the inserter instrument 30 when the inserter instrument is attached to the trial implant 522.

As shown in FIG. 9B, the first mating portion 538 defines a primary articulation interface, such as an inferior articulating surface 580 and an auxiliary articulating interface, such as an engagement feature 584 for coupling the superior plate 100 to the inferior plate 104. The inferior surface 580 is curved along the longitudinal direction and is concave. As shown in FIG. 9B, the engagement feature 584 extends down from the inferior surface 580 and defines a T-shaped protrusion 588. In particular, the engagement feature 584 includes a first member 592 that extends down from the inferior surface 580 and a second member 596 that extends in the lateral direction from an end of the first member 592. As shown, the T-shaped protrusion 588 is disposed proximate to the center of the inferior surface 580.

As shown in FIGS. 9A-9B, the inferior plate 530, includes a generally oval shaped body 600 having a second mating portion 604 incorporated into a top or superior side of the body 600. As shown, the body 600 defines a lower or inferior, or outer transverse engagement surface 608 configured to contact the superior endplate of the inferior vertebral body 10b, a proximal surface 612 and a distal surface 616. The inferior surface 608 is generally flat and includes a pair of spaced apart rails or grooves 620 disposed along the longitudinal direction for receiving lower arms of a distractor instrument, such as the arms of the distractor instrument 400 (shown in FIG. 10).

As shown in FIGS. 9A-9B, the proximal surface 612 of the body 600 defines a coupling member 624 that is configured to couple the trial implant 522 to an inserter instrument, such as the inserter instrument 30. As shown, coupling member 624 includes a bore 628 that extends longitudinally into the proximal surface 612 of the inferior plate 530. The bore 628 is sized to receive external threads of a shaft of an inserter inst. The bore 628 is configured to mate with a coupling member of an inserter instrument, such as the coupling member of the inserter instrument 30, to thereby couple the trial implant 522 to the inserter instrument.

As shown in FIG. 9A, the second mating portion 214 defines a primary articulation interface, such as a superior articulating surface 632 and an auxiliary articulation interface, such as an engagement feature 636 for coupling the inferior plate 530 to the superior plate 526. The superior surface 632 is curved along the longitudinal direction and is convex. The convex superior surface 632 corresponds to the concave inferior surface 608 of the superior plate 526. As shown in FIG. 9A, the engagement feature 636 is defined in the superior surface 632 and includes a slot 640 that extends into the superior surface 632 and along the superior surface 632 in the longitudinal direction. The engagement feature 636 further includes an opening 644 at a proximal end of the slot 640. The opening 644 has a lateral width that is greater than the lateral width of the slot 640 and configured to receive the engagement feature 584 of the superior plate 526. In particular the opening 644 has a width that is capable of receiving the second member 596 of the superior plate's engagement feature 584. As shown in FIG. 9C, the engagement feature 636 of the inferior plate 530 further includes a cavity 650 below the slot 640. The cavity 650 has a lateral width that is approximately equal to the lateral width of the opening 644, and extends in the longitudinal direction. As shown, the cavity 650 includes an upper concave surface 654 and a lower convex surface 658. The surfaces 654 and 658 have similar arcs as the curved inferior surface 580 and the curved superior surface 632 respectively. Therefore, the superior plate 526 can move relative to the inferior plate 530 along the arc defined by the superior and inferior surfaces 580, 632, while at the same time remaining coupled to each other.

Figure 10B:
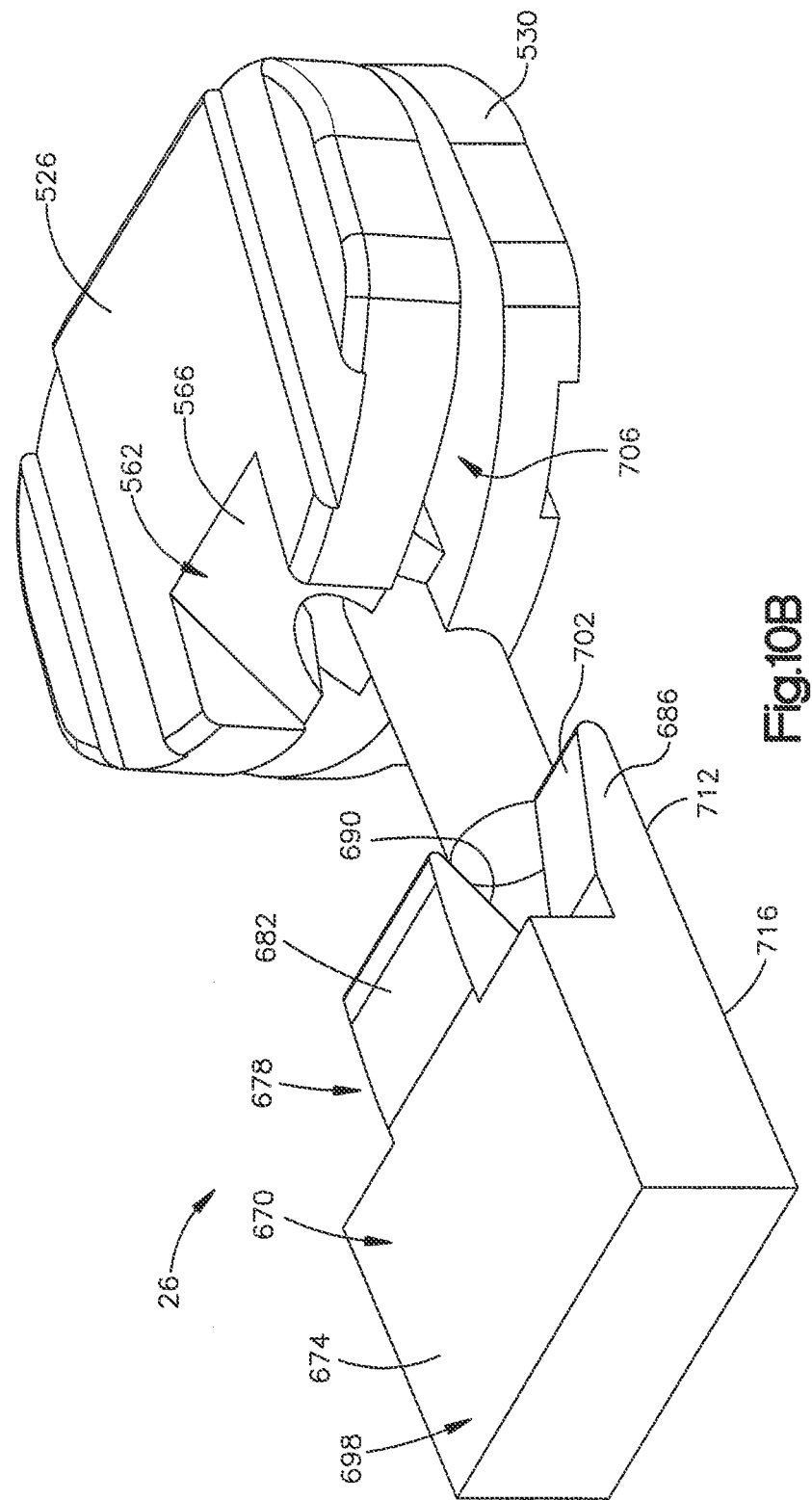
FIG. 10B is another perspective view of the trial implant system shown in FIG. 10A.

As shown in FIGS. 10A-10C, the inserter instrument may include a locking block having a locking mechanism configured to restrict movement of the superior plate 526 relative to the inferior plate 530. As shown, the inserter instrument may include a locking block 670 having body 674 and a locking mechanism 678 extending distally from the body 674. As shown, the locking mechanism includes an upper wedge 682 and two lower wedges 686. The upper wedge 682 includes an angled bottom surface 690 that extends up as it extends distally from the body 674. The wedge 682 is configured to be received by the recess 562 of the superior plate 526, while the angled bottom surface 690 is configured to smoothly engage the angled bottom surface 566 of the recess 562. As shown, the wedge 682 is centrally located and has an upper surface 694 that is flush with an upper surface 698 of the body 674. The two lower wedges 686 each include an angled upper surface 702 that extend down as they extend distally from the body 674. The lower wedges 686 are configured to engage a space 706 defined between the superior plate 526 and the inferior plate 530. As shown, the lower wedges 686 are located on either side of the upper wedge 682 and include lower surfaces 712 that are flush with a lower surface 716 of the body 674.

As shown in FIG. 10C, when the locking mechanism 678 engages the locking 558 of the trial implant 522, the superior plate 526 is restricted from moving relative to the inferior plate 530. As shown, to restrict the movement, the upper wedge 682 of the locking block 670 engages the recess 562 of the superior plate 526 and the lower wedges 686 engage the space or gap 706 between the superior plate 526 and the inferior plate 530 to thereby wedge the superior plate 526 between the upper wedge 682 and the lower wedges 686 and restrict the superior plate's movement.

Figure 11A:
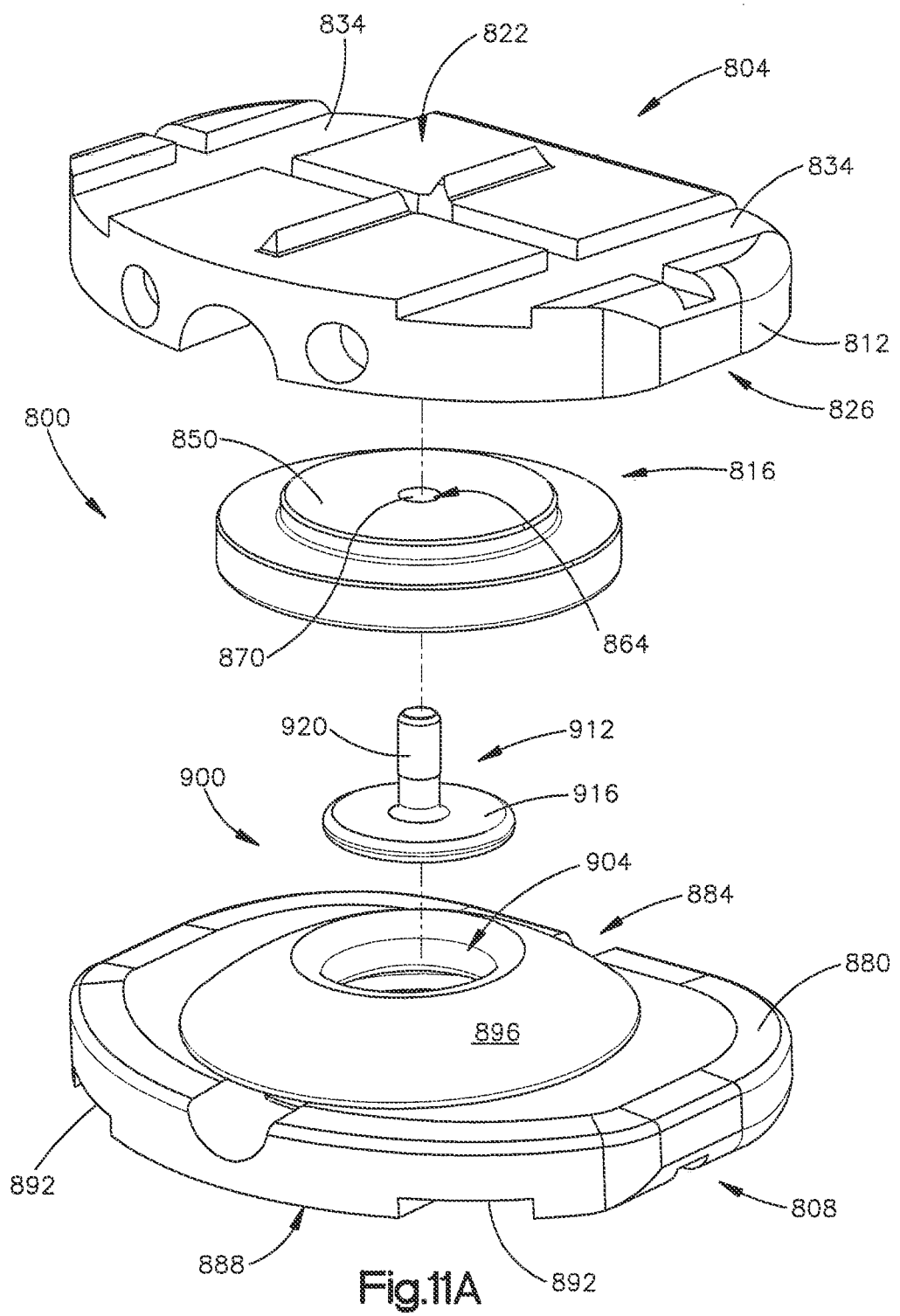
FIG. 11A is an exploded perspective view of a trial implant system including a trial implant having a superior plate and an inferior plate in accordance with another embodiment.

As shown in FIGS. 11A-11F, the trial implant may be configured to move in more that one direction. For example, as shown, a trial implant 800 includes a superior plate 804 coupled to an inferior plate 808, such that the superior plate 804 is capable of moving in all directions relative to the inferior plate 808, as shown in FIGS. 11B and 11C.

Figure 11D:
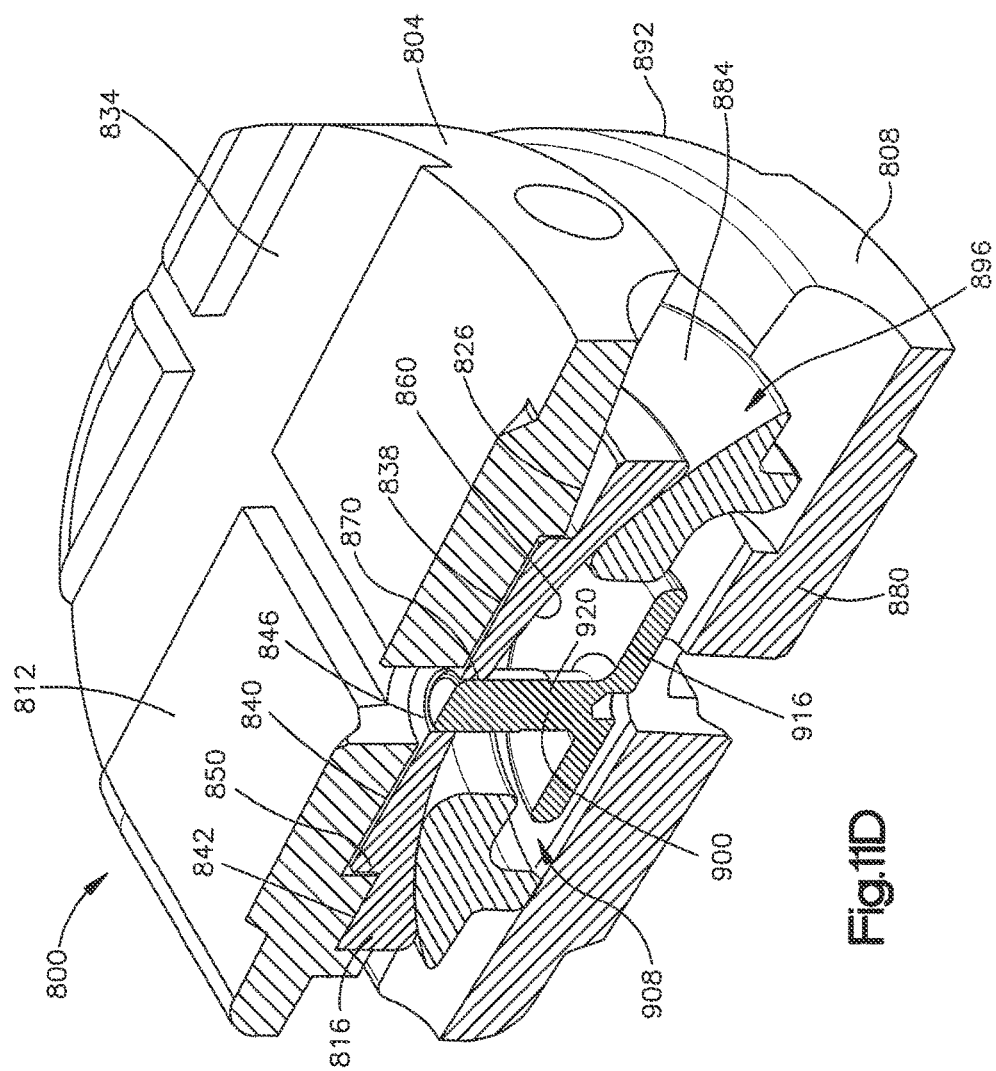
FIG. 11D is a cut-away perspective view of the trial implant shown in FIG. 11A.

As shown in FIGS. 11A and 11D, the superior plate 804 includes a generally oval shaped body 812 having a first mating portion 816 coupled to a bottom or inferior side of the body 812. As shown, the body 812 defines an upper or superior, or outer transverse engagement surface 822 configured to contact the inferior endplate of the superior vertebral body 10a, and a bottom surface 826 configured to mate with the first mating portion 816. The superior surface 822 includes a pair of spaced apart rails or grooves 834 disposed along the longitudinal direction for receiving arms of a distractor instrument, such as the distractor instrument 400 shown in FIG. 10.

As shown in FIG. 11D, the bottom surface 826 of the superior plate's body 812 defines a centralized recess 838. As shown, the recess 838 is circular, though it should be understood that any shape may be used. A center portion 840 of the centralized recess 838 is deeper than a periphery of the recess 838. Thus, the periphery of the recess defines a peripheral shoulder 842 that extends around the center portion 840 of the recess 838. Proximate to a center of the centralized recess 838 is a bore 846 that extends transversely into the body 812.

As shown in FIGS. 11A and 11D, the first mating portion 816 is separate from the body 812 and is coupleable to the bottom surface 826 of the body 812. The first mating portion 816 includes a circular protrusion 850 that extends in an upward direction. As shown in FIG. 11D, the circular protrusion 850 of the first mating portion 816 mates with the center portion of the circular recess 838 of the body 812, while the remainder of the first mating portion 816 mates with the shoulder 842 of the recess 838. The first mating portion 816 further defines a primary articulation interface, such as an inferior articulating surface 860 and an auxiliary articulation interface, such as an engagement feature 864 for coupling the superior plate 804 to the inferior plate 808. The inferior surface 860 is curved and forms a concave hemisphere. As shown in FIGS. 11A and 11D, the engagement feature 864 is a bore 870 that extends into the inferior surface 580 and through a top side of the protrusion 850. As shown, the bore 870 is disposed proximate to the center of the inferior surface 860 and aligns with the 846 that extends into the recess 838 of the superior plate body 812.

As shown in FIGS. 11A and 11D, the inferior plate 808, includes a generally oval shaped body 880 having a second mating portion 884 incorporated into a top or superior side of the body 880. As shown, the body 880 defines a lower or inferior, or outer transverse engagement surface 888 configured to contact the superior endplate of the inferior vertebral body 10b. The inferior surface 888 includes a pair of spaced apart rails or grooves 892 disposed along the longitudinal direction for receiving lower arms of a distractor instrument, such as the lower arms of the distractor instrument 400 (shown in FIG. 10).

As shown in FIGS. 11A and 11D, the second mating portion 884 defines a primary articulating interface, such as a superior articulating surface 896 and an auxiliary articulating interface, such as an engagement feature 900 for coupling the inferior plate 808 to the superior plate 804. The superior surface 896 is curved and forms a convex hemisphere. The convex superior surface 896 corresponds to and mates with the concave inferior surface 860 of the superior plate 804. As shown, the second mating portion 884 further includes a bore 904 that extends through the superior surface 896 and into a cavity 908 defined within the second mating portion 884. The cavity 908 is circular and has a diameter that is greater than the diameter of the bore 904 that leads into the cavity 908. The second mating portion 884 further includes a plug 912 that is separate from the remainder of the second mating portion 884. As shown, the plug 912 includes a disc 916 and a pin 920 that extends up from an upper surface of the disc 916. As shown in FIG. 11D, the plug 912 is disposed within the cavity 908 of the second mating portion 884. In particular, the disc 916 of the plug 912 is placed within the cavity 908 while the pin 920 extends up through the bore 904 of the second mating portion 884. As shown in FIG. 11D, the pin 920 extends through the bore 904 of the second mating portion 884, through the bore 870 of the first mating portion 816 and into the bore 846 of the superior plate's body 812 to thereby couple the inferior plate 808 to the superior plate 804. In this way, the cavity 908, the bore 904, and the plug 912 define the engagement feature 900 of the second mating portion 884.

As shown in FIGS. 11B, 11C, 11E, and 11F, the superior plate 804 is configured to move relative to the inferior plate 808. For example, the superior plate 804 may be moved to a first position as shown in FIGS. 11B and 11E, in which the superior plate 804 is moved laterally to the left about the inferior plate 808. In particular, the plug 912 rocks to the left within the cavity 908 while the inferior surface 860 of the superior plate 804 slides to the left along the superior surface 896 of the inferior plate 808. As shown in FIGS. 11C and 11F, the superior plate 804 may be moved to a second position, in which the superior plate 804 is moved laterally to the right about the inferior plate 808. In particular, the plug 912 rocks to the right within the cavity 908 while the inferior surface 860 of the superior plate 804 slides to the right along the superior surface 896 of the inferior plate 808. Though not shown, the superior plate 804 may also be moved to a third position in which the superior plate 804 is moved distally about the inferior plate 808, and to a fourth position in which the superior plate 804 is moved proximally about the inferior plate 808, furthermore, the superior plate 804 may be moved to additional positions between any of the first, second, third, and fourth positions. That is, the hemispherically curved inferior and superior surfaces 860, 896, allow the superior plate 804 to move along an arc in any direction relative to the inferior plate 808.

Figure 12B:
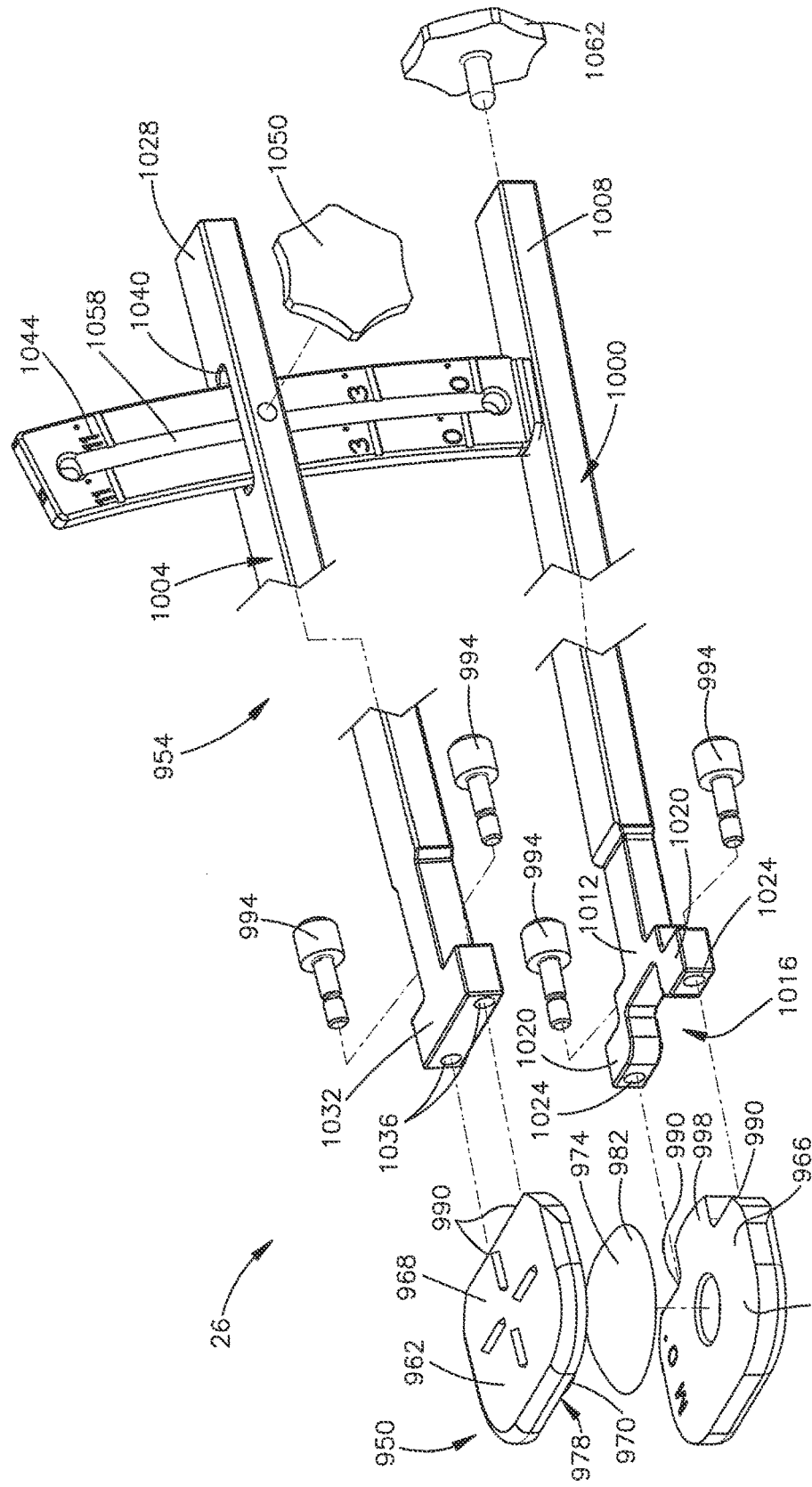
FIG. 12B is an exploded assembly view of the trial implant system shown in FIG. 12A.

In another embodiment and in reference to FIGS. 12A and 12B, the trial implant system 26 may include a trial implant 950 and an inserter instrument 954 for inserting the trial implant 950 into an intervertebral space. The trial implant 950 is similar to the trial implant 800 shown in FIGS. 11A-11F and is configured to have different heights, while the inserter instrument 954 includes a protractor member 958 configured to measure the required angle on the plates to fill the lordotic angle between the vertebral bodies.

As shown in FIG. 12B, the trial implant 950 includes a superior plate 962 coupled to an inferior plate 966. As shown, the superior plate 962 and the inferior plate 966 include corresponding primary articulating interfaces, such as hemispherical articulating surfaces 970, 974. In particular, the superior plate 962 includes a body 968 coupled to a first mating portion 978 having a concave inferior surface 970, while the inferior plate 966 includes a body 980 coupled to a second mating portion 982 having a convex superior surface 974 configured to mate with the inferior surface 970. As shown, the second mating portion 982 is separable from inferior plate body 980. Therefore, the inferior plate 966 may be fit with different second mating portions 982 having different heights to cover various disc heights.

As shown in FIG. 12B, the superior plate 962 and the inferior plate 966 each include a coupling member such as a pair bores 990 extending into a proximal surface of each plate 962 and 966. The bores 990 are configured to receive fixation elements, such as bolts 994 to thereby couple the inserter instrument 954 to the trial implant 950. The inferior plate 966 further includes a square protrusion 998, that extends proximally from its proximal surface.

As shown in FIGS. 12A and 12B, the inserter instrument 954 includes a lower arm 1000, an upper arm 1004, and a measuring member, such as a protractor member 958 extending between the lower arm 1000 and the upper arm 1004. As shown, the lower arm 1000 includes a lower arm body 1008 that is elongate in the longitudinal direction and a coupling member 1012 that extends distally from the body 1008. As shown, the coupling member 1012 defines a recess 1016 and a pair of wings 1020 that extend laterally out from the recess 1016. Each wing 1020 includes a bore 1024 that extends through the wing 1020 in the longitudinal direction. Each bore 1024 is configured to receive a bolt 994 to thereby couple the lower arm 1000 to the inferior plate 966. When the lower arm 1000 is coupled to the inferior plate 966 the protrusion 998 is received by the recess 1016 defined by the lower arm's coupling member 1012. Similar to the lower arm 1000, the upper arm 1004 includes an upper arm body 1028 that is elongate in the longitudinal direction and a coupling member 1032 that extends distally from the body 1028. As shown, the coupling member 1032 includes a pair of bores 1036 that extend through the coupling member 1032 in the longitudinal direction. Each bore 1036 is configured to receive a bolt 994 to thereby couple the upper arm 1004 to the superior plate 964.

As shown in FIG. 12B, the upper arm 1004 further includes a transverse slot 1040 that extends through the upper arm body 1028 proximate to the proximal end of the arm body 1028. The protractor member 958 is rigidly coupled to the lower arm 1000 and extends up toward the upper arm 1004 and through the slot 1040 defined by the upper arm body 1028. The protractor member 958 is curved and includes indicia 1044 for determining the angle on the plates to fill the lordotic angle between the vertebral bodies. Thus, the upper arm 1004 is capable of rotating through an arc defined by the protractor body 958. Initially the upper arm 1004 should be rigidly coupled to the lower arm 1000 while the trial implant 950 is being inserted into the intervertebral space. To lock the upper arm 1004 relative to the lower arm 1000, the inserter instrument 954 further includes a lock screw 1050 configured to extend through a lateral bore 1054 defined in the upper arm body 1028 and into a slot 1058 defined by the protractor member 958.

In operation, the trial implant 950 is initially coupled to the inserter instrument 954 such that the upper arm 1004 is rigidly coupled to the lower arm 1000. The trial implant 950 may be inserted into the intervertebral space by hammering a proximal end 1062 of the lower arm 1000. Once properly inserted, the lock screw 1050 is released to allow the upper arm 1004 to rotate. The angle between the upper arm 1004 and the lower arm 1000 can be read from the indicia 1044 of the protractor member 958 to thereby determine the required angle on the plates to fill the lordotic angle between the vertebral bodies.

Figure 13C:
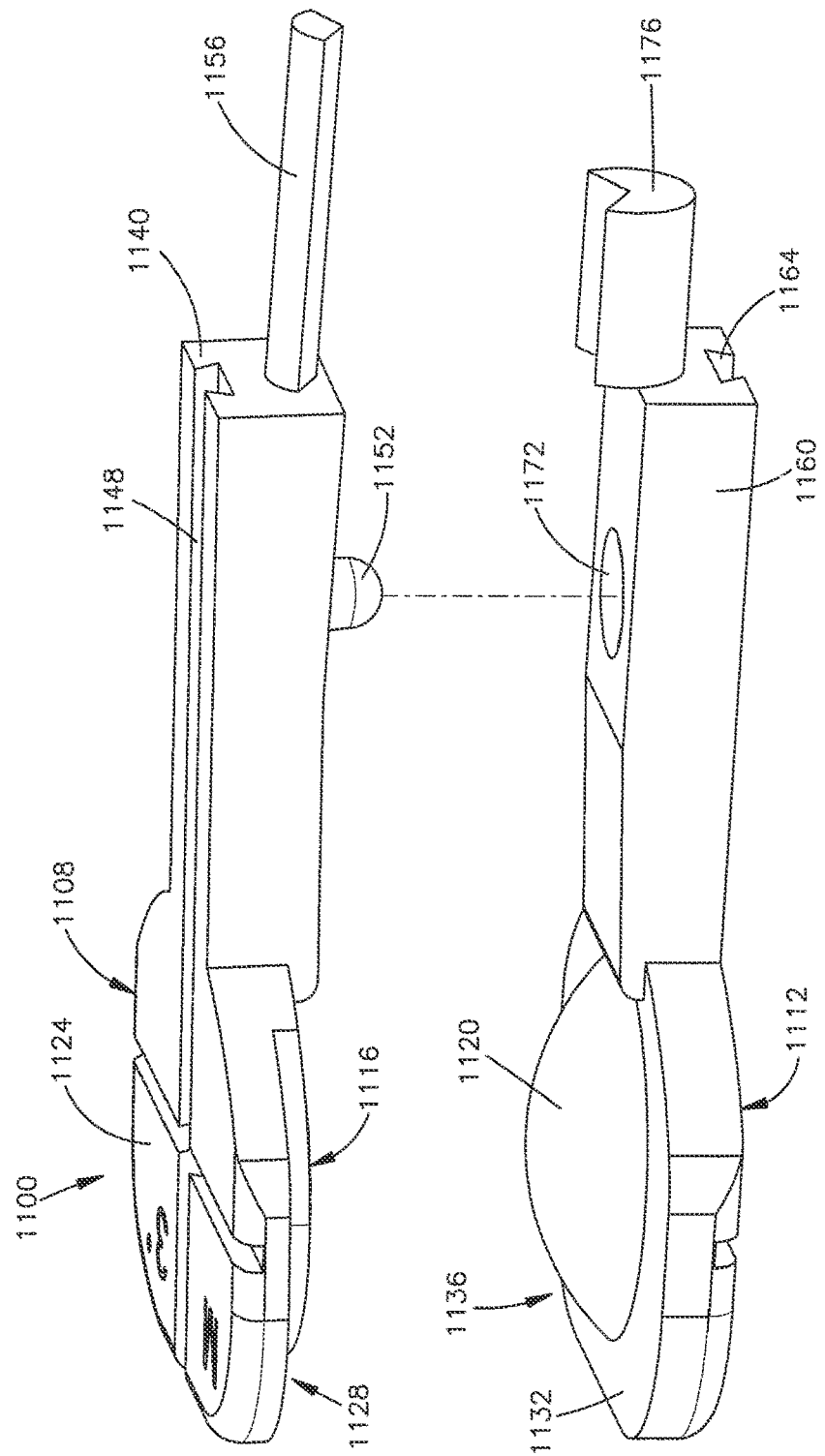
FIG. 13C is another exploded assembly view of the trial implant shown in FIG. 13A.

In another embodiment and in reference to FIGS. 13A-13C, the trial implant system 26 may include a trial implant 1100 and an inserter instrument 1104 for inserting the trial implant 1100 into an intervertebral space. The trial implant 1100 and the inserter instrument 1104 are configured to determine the proper angle of the plates.

As shown in FIG. 13C, the trial implant 1100 includes a superior plate 1108 coupled to an inferior plate 1112. As shown, the superior plate 1108 and the inferior plate 1112 include corresponding primary articulation interfaces, such as hemispherical articulating surfaces 1116, 1120. In particular, the superior plate 1108 includes a body 1124 coupled to a first mating portion 1128 having a concave inferior surface 1116, while the inferior plate 1112 includes a body 1132 coupled to a second mating portion 1136 having a convex superior surface 1120 configured to mate with the inferior surface 1116.

As shown, the superior plate 1108 includes an elongate member 1140 extending proximally from the body 1124. A shown, the elongate member 1140 includes a dove tailed recess 1148 extending into a top surface of the elongate member 1140 and longitudinally through the proximal end of the elongate member 1140 and out the distal end of the body 1124. The elongate member 1140 further includes a protrusion 1152 that extends down from a bottom surface of the member 1140. As shown in FIG. 13C, the superior plate 1108 further includes a protrusion 1156 that extends proximally from a proximal surface of the elongate member 1140. As shown, the protrusion 1156 defines a portion of a cylinder.

Like the superior plate 1108, the inferior plate 1112 includes an elongate member 1160 extending proximally from the body 1132. As shown, the elongate member 1160 includes a dove tailed recess 1164 extending into a bottom surface of the elongate member 1160 and longitudinally through the proximal end of the elongate member 1160 and out the distal end of the body 1132. The elongate member 1160 further includes a bore 1172 extending into a top surface of the member 1160. As shown, the bore 1172 is configured to receive the protrusion 1152 of the superior plate 1108 to restrict longitudinal movement of the superior plate 1108 relative to the inferior plate 1112. As shown in FIG. 13C, the inferior plate 1112 further includes a protrusion 1176 that extends proximally from a proximal surface of the elongate member 1160. As shown, the protrusion 1176 defines a portion of a cylinder. When the superior plate 1108 is mated with the inferior plate 1112, the protrusion 1156 of the superior plate 1108 and the protrusion 1176 of the inferior plate 1112 mate to define a complete cylinder having external threads to thereby define a coupling member of the trial implant 1100. As shown, however, the protrusion 1156 of the superior plate 1108 has a longitudinal length that is greater than the longitudinal length of the protrusion 1176 of the inferior plate 1112.

As shown in FIGS. 13A and 13B, the inserter instrument 1104 includes a cylindrical body 1180 that is elongate in the longitudinal direction. A distal end of the body 1180 defines a bore 1184 having internal threads. The bore 1184 is configured to receive the completed cylinder of the trial implant 1100 to thereby couple the inserter instrument 1104 to the trial implant 1100. The inserter instrument further includes a second body 1188 coupled to a proximal end of the body 1180 that is elongate in the transverse direction. The second body member 1188 includes a pair of slots 1192 that through the second body 1180 and along the body 1180 in the transverse direction. As shown, the slots 1192 are open at their respective ends.

As shown in FIGS. 13A and 13B, the inserter instrument 1104 further includes a pair of mono-chisels 1200. Each mono-chisel 1200 includes a chisel body 1204 that is elongate in the longitudinal direction. Extending from a distal end of the chisel body 1204 is a chisel portion 1208. Each chisel portion 1208 includes a dove tail 1212 extending along its longitudinal length. The dove tails 1212 are configured to engage the dove tailed recesses 1148, 1164 of the superior and inferior plates. Each chisel 1200 includes an edge 1220 on an opposite side of the chisel portion's dove tail 1212. As shown, each chisel 1200 extends through a respective slot 1192 of the second body member 1180. Thus, as the superior plate 1108 or the inferior plate 1112 rotate, the chisels 1200 will slide within their respective slots 1192.

In operation, the trial implant 1100 is coupled to the inserter instrument 1104, and then the trial implant 1100 is inserted into the intervertebral disc space. The body 1180 of the inserter instrument 1104 is then unscrewed from the trial implant 1100 to release the superior and inferior plates 1108, 1112. If the chosen angles are correct and the disc removal is properly done, the superior and inferior plates 1108, 1112 will not move, but if one of them is not correct (for the angles are too small) the superior plate 1108 will rotate about the articulating surface 1120 of the inferior plate 1112, showing the need for a greater angle. In this case the trial implant 1100 should be removed. To this end, the body 1180 of the inserter instrument 1104 should be translated forward to initially grab the protrusion 1156 of the superior plate 1108. As the body 1180 is translated further forward the protrusion 1156 is pushed down until it mates with the protrusion 1176 of the inferior plate 1112 to complete the cylindrical shape of the trial implant's coupling member. By rotating the body 1180 the inserter instrument 1104 will be reattached to the trial implant 1100. Now the trial implant 1100 may be removed and the new one will be selected to be implanted. This process may be repeated until the correct trial implant has been selected. To achieve the correct angles on the superior and inferior plates 1108, 1112, the surgeon may start with lower angles and build up by truing higher angles until an optimum angle is achieved. Once the correct angles are determined the two chisels 1200 may be used to perform keel cuts in the vertebral bodies. Because the chisels 1200 are parallel to the superior and inferior plates 1108, 1112. During the procedure the dove tailed recesses 1148, 1164 of the superior and inferior plates may be used in X-ray images as guides for determining the midline of the vertebral bodies.

It should be understood that any of the trial implants disclosed may be sold as a kit including various sizes of the trial implants, as well as a kit of trial implants and permanent implants. Furthermore, any of the trial implants may be sold as a kit with any of the inserter instruments including chisels that are disclosed.

It should also be understood that the disclosed trial implants illustrate that trial implants usable in connection with any of the trial implant systems described herein can be configured as to provide a range of numerous possible geometries and configurations. While the trial implant systems of the present invention have been described in reference to surgical procedures for replacing a damaged intervertebral disc with a total disc replacement implant, it is understood that the teachings of the present invention are easily configurable for surgical procedures for fusing a damaged disc space using an interbody spacer. It should also be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. It is understood, therefore, that this invention is not limited to the particular embodiments disclosed, but is intended to cover modifications within the spirit and scope of the present disclosure.

What is claimed:

1. A method of determining a dimension of a permanent intervertebral implant, the method comprising the steps of:
    coupling a lower arm of an inserter instrument to an inferior plate of a trial implant and coupling an upper arm of the inserter instrument to a superior plate of the trial implant, wherein the superior plate is supported by the inferior plate;
    engaging a lock of the inserter instrument thereby temporarily restricting angulation of the superior plate relative to the inferior plate;
    after the engaging step, inserting the trial implant into an intervertebral space that is between a superior vertebral body and an inferior vertebral body;
    after the inserting step, disengaging the lock thereby discontinuing the step of temporarily restricting, thereby allowing the superior plate and the inferior plate to angulate with respect to each other, wherein the disengaging step is performed while the inserter instrument is coupled to both the inferior plate and the superior plate of the trial implant; and after the disengaging step, angulating the upper arm relative to the lower arm;

after the inserting step, measuring relative angulation between the superior plate and the inferior plate with a protractor member disposed between the lower arm and the upper arm.

2. The method of claim 1, wherein the coupling step further comprises engaging a first engagement feature of the inserter instrument with one of the superior and inferior plates of the trial implant.

3. The method of claim 2, wherein the coupling step further comprises coupling a second engagement feature of the inserter instrument with the other of the inferior and superior plates.

4. The method of claim 1, wherein the inserting step further comprises engaging an outer surface of the superior plate with an inferior surface of the superior vertebral body and engaging an outer surface of the inferior plate with a superior surface of the inferior vertebral body.

5. The method of claim 4, wherein the inserting step further comprises placing the trial implant into the intervertebral space, the intervertebral space being disposed between the inferior surface of the superior vertebral body and the superior surface of the inferior vertebral body.

6. The method of claim 1, further comprising the step of removing the trial implant from the intervertebral space after the measuring step.

7. The method of claim 6, further comprising, after the removing step, the step of surgically inserting a permanent articulating total disc replacement implant into the intervertebral space, the permanent implant having the measured angulation between the superior plate and the inferior plate.

8. The method of claim 1, further comprising the step of articulating the superior plate relative to the inferior plate about an articulating interface at a juncture between the superior and inferior plates.

9. The method of claim 8, wherein the trial implant is inserted along an insertion direction, and wherein the articulating step further comprises restricting the articulation to an arc that is partially defined by the insertion direction.

10. The method of claim 1, wherein the inserting step is performed by the a lower arm of the inserter instrument.

11. The method of claim 10, wherein the discontinuing step further comprises articulating the superior plate relative to the inferior plate about a hemispherical articulating interface at a juncture between the superior and inferior plates.

12. The method of claim 11 further comprising the step of removably attaching the hemispherical articulating surface to an inner portion of the inferior plate, wherein the removably attaching step is performed prior to the discontinuing step.

13. The method of claim 1 further comprising the steps of:
selecting a permanent intervertebral implant having the angulation;
after the measuring step, removing the trial implant from the intervertebral space; and
inserting the permanent intervertebral implant into the intervertebral space.

14. A method of determining a dimension of a permanent intervertebral implant, the method comprising the steps of:
coupling a lower arm of an inserter instrument to an inferior plate of a trial implant, and coupling an upper arm of the inserter instrument to a superior plate of the trial implant, the superior plate supported by the inferior plate at a hemispherical articulating interface;
engaging a locking screw of the inserter instrument thereby temporarily restricting angulation of the superior plate relative to the inferior plate;
after the step of temporarily restricting, inserting the trial implant into an intervertebral space that is partially defined by a superior vertebral body and an inferior vertebral body;
after the inserting step, discontinuing the step of temporarily restricting, thereby allowing the superior plate and the inferior plate to angulate with respect to each other, wherein the discontinuing step further comprises articulating the superior plate relative to the inferior plate, wherein the discontinuing step is performed while the inserter instrument is coupled to both the inferior plate and the superior plate of the trial implant; and
after the inserting step, measuring an angle defined by the superior plate and the inferior plate.

15. The method of claim 14, wherein the inserting step is performed by hammering the lower arm of the inserter instrument.

16. The method of claim 14, further comprising the step of removably attaching the hemispherical articulating interface to an inner portion of the inferior plate, wherein the removably attaching step is performed prior to the discontinuing step.

17. A method of determining a dimension of a permanent intervertebral implant, the method comprising the steps of:
coupling an inserter instrument to an inferior plate of a trial implant and a superior plate of the trial implant, wherein the superior plate is supported by the inferior plate;
engaging a lock of the inserter instrument thereby temporarily restricting angulation of the superior plate relative to the inferior plate;
after the engaging step, inserting the trial implant into an intervertebral space that is between a superior vertebral body and an inferior vertebral body, wherein the lower arm is coupled to the inferior plate;
after the inserting step, disengaging the lock thereby discontinuing the step of temporarily restricting, thereby allowing the superior plate and the inferior plate to angulate with respect to each other, wherein the disengaging step is performed while the inserter instrument is coupled to both the inferior plate and the superior plate of the trial implant, wherein the discontinuing step further comprises articulating the superior plate relative to the inferior plate about a hemispherical articulating interface at a juncture between the superior and inferior plates; and
after the inserting step, measuring relative angulation between the superior plate and the inferior plate.

18. The method of claim 17, further comprising the step of removably attaching the hemispherical articulating surface to an inner portion of the inferior plate, wherein the removably attaching step is performed prior to the discontinuing step.

* * * * *